United States Patent
Oba et al.

(10) Patent No.: US 8,971,749 B2
(45) Date of Patent: Mar. 3, 2015

(54) OPTICAL SENSOR AND IMAGE FORMING APPARATUS

(71) Applicants: Yoshihiro Oba, Miyagi (JP); Satoru Sugawara, Miyagi (JP); Toshihiro Ishii, Miyagi (JP); Fumikazu Hoshi, Miyagi (JP)

(72) Inventors: Yoshihiro Oba, Miyagi (JP); Satoru Sugawara, Miyagi (JP); Toshihiro Ishii, Miyagi (JP); Fumikazu Hoshi, Miyagi (JP)

(73) Assignee: Ricoh Company, Ltd., Tokyo (JP)

(*) Notice: Subject to any disclaimer, the term of this patent is extended or adjusted under 35 U.S.C. 154(b) by 121 days.

(21) Appl. No.: 13/768,265

(22) Filed: Feb. 15, 2013

(65) Prior Publication Data

US 2013/0216247 A1 Aug. 22, 2013

(30) Foreign Application Priority Data

Feb. 17, 2012 (JP) ................................ 2012-032259

(51) Int. Cl.
G03G 15/00 (2006.01)
G01N 21/47 (2006.01)
G01N 21/55 (2014.01)
G03G 13/00 (2006.01)

(52) U.S. Cl.
CPC ............ *G01N 21/4738* (2013.01); *G01N 21/55* (2013.01); *G03G 13/00* (2013.01); *G03G 15/5029* (2013.01); *G03G 15/6591* (2013.01); G03G 2215/00616 (2013.01)
USPC ................. 399/74; 399/49; 356/369

(58) Field of Classification Search
USPC ....................... 399/49, 74; 356/369
See application file for complete search history.

(56) References Cited

U.S. PATENT DOCUMENTS

| | | | | |
|---|---|---|---|---|
| 3,931,525 A | * | 1/1976 | Clarke | 250/559.49 |
| 4,701,052 A | * | 10/1987 | Schoen, Jr. | 356/369 |
| 4,796,065 A | * | 1/1989 | Kanbayashi | 399/60 |
| 5,481,085 A | * | 1/1996 | Kovacevic et al. | 219/130.01 |
| 5,835,220 A | * | 11/1998 | Kazama et al. | 356/369 |
| 6,393,228 B2 | * | 5/2002 | Hisano | 399/49 |
| 6,633,734 B2 | * | 10/2003 | Maebashi et al. | 399/49 |
| 6,657,736 B1 | * | 12/2003 | Finarov et al. | 356/625 |
| 6,731,886 B2 | | 5/2004 | Takeda | |
| 6,853,817 B2 | * | 2/2005 | Suzuki | 399/49 |
| 7,181,148 B2 | * | 2/2007 | Sakai et al. | 399/49 |
| 7,899,348 B2 | * | 3/2011 | Maruyama et al. | 399/48 |
| 7,978,739 B2 | | 7/2011 | Sugawara et al. | |
| 8,035,676 B2 | | 10/2011 | Harasaka et al. | |
| 8,111,725 B2 | | 2/2012 | Ishii et al. | |
| 2001/0028804 A1 | * | 10/2001 | Hisano | 399/49 |
| 2002/0041770 A1 | * | 4/2002 | Nakazato et al. | 399/49 |

(Continued)

FOREIGN PATENT DOCUMENTS

JP 2002-340518 11/2002

*Primary Examiner* — G. M. Hyder
(74) *Attorney, Agent, or Firm* — Cooper & Dunham LLP

(57) ABSTRACT

An optical sensor is disclosed. The optical sensor includes an irradiating system which irradiates a linearly polarized light; a first photodetecting system including a first photodetector which is arranged on an optical path of a light which is specularly reflected from a subject; a second photodetecting system including an optical element which is arranged on an optical path of a light which is diffuse reflected from the subject within an incident face in the subject and which separates a linearly polarized component in a second polarizing direction which is orthogonal to a first polarizing direction and a second photodetector which receives a light separated by the optical element, wherein an angle of taking in the light in the first photodetector and an angle of taking in the light in the second photodetector are mutually different.

12 Claims, 34 Drawing Sheets

(56) References Cited

U.S. PATENT DOCUMENTS

| | | | |
|---|---|---|---|
| 2002/0098004 A1* | 7/2002 | Hama et al. | 399/49 |
| 2004/0183880 A1* | 9/2004 | Kito | 347/101 |
| 2004/0208663 A1* | 10/2004 | Sakai et al. | 399/49 |
| 2008/0062406 A1* | 3/2008 | Finarov et al. | 356/73 |
| 2008/0292360 A1* | 11/2008 | Hirai | 399/220 |
| 2009/0034990 A1* | 2/2009 | Nakazato et al. | 399/9 |
| 2009/0295902 A1 | 12/2009 | Sato et al. | |
| 2010/0182602 A1* | 7/2010 | Urano et al. | 356/369 |
| 2010/0328747 A1 | 12/2010 | Jikutani et al. | |
| 2011/0037825 A1 | 2/2011 | Jikutani et al. | |
| 2011/0109713 A1 | 5/2011 | Yamaguchi et al. | |
| 2011/0115872 A1 | 5/2011 | Harasaka et al. | |
| 2011/0170155 A1 | 7/2011 | Jikutani et al. | |
| 2011/0211869 A1 | 9/2011 | Shouji et al. | |
| 2011/0228035 A1 | 9/2011 | Ishii et al. | |
| 2011/0261139 A1 | 10/2011 | Hoshi et al. | |
| 2011/0267415 A1 | 11/2011 | Ohba et al. | |
| 2012/0121297 A1 | 5/2012 | Jikutani et al. | |
| 2012/0134693 A1* | 5/2012 | Hoshi et al. | 399/45 |
| 2013/0216245 A1* | 8/2013 | Hoshi et al. | 399/45 |
| 2013/0216246 A1* | 8/2013 | Hoshi et al. | 399/45 |
| 2013/0228674 A1* | 9/2013 | Oba et al. | 250/225 |

* cited by examiner

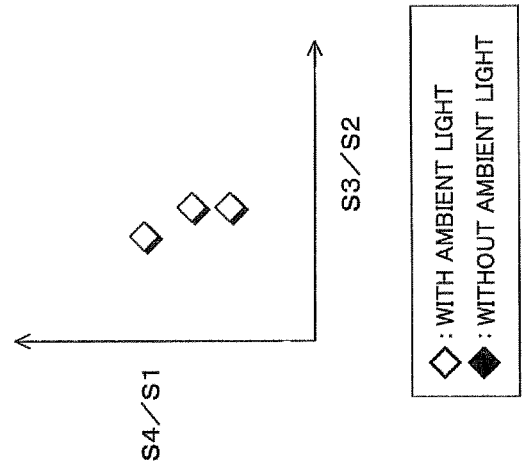
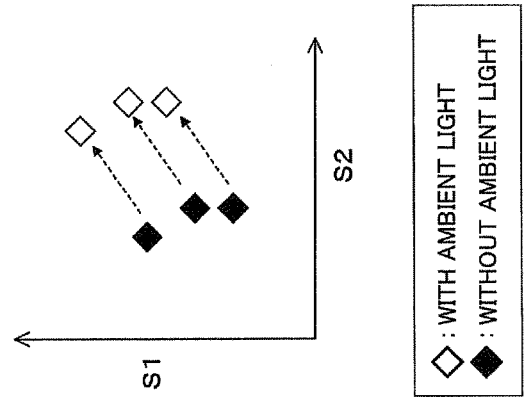

OPTICAL SENSOR AND IMAGE FORMING APPARATUS

TECHNICAL FIELD

The present invention relates to optical sensors and image forming apparatuses and particularly to optical sensors which are suitable for specifying an object and image forming apparatuses which include the optical sensors.

BACKGROUND ART

An image forming apparatus such as a digital copying machine, a laser printer, etc., forms an image by transferring a toner image onto a surface of a recording medium including printing paper, and heating and pressurizing at predetermined conditions to fix the toner image. What need to be taken into account in image forming are conditions of pressure and thermal dose at the time of fixing. In particular, in order to conduct a high quality image forming, it is necessary to set fixing conditions individually according to the recording medium.

This is because image quality in the recording medium is largely affected by the quality of material, thickness, humidity, smoothness, and coating conditions thereof. For example, with respect to the smoothness, a fixing rate of toner on a concave portion in irregularities of the printing sheet surface decreases depending on the fixing conditions. Thus, uneven coloring occurs unless fixing is performed with proper conditions which are dependent on the recording medium.

Moreover, in conjunction with progress in image forming apparatuses and diversification in representation methods in recent years, there are at least several hundred types of recording media for printing paper alone. Moreover, for the respective types, there are brands which widely vary depending on differences in a specification such as a paper weight, a thickness, etc. In order to form high quality images, it is necessary to minutely set fixing conditions depending on these individual brands.

Moreover, in recent years, brands are increasing also for plain paper; coated paper such as gloss coated paper, mat coated paper, and art coated paper; a plastic sheet; and special paper, on which surface an emboss treatment is applied.

In the present-day image forming apparatus, a user himself must set the fixing conditions at the time of printing. Therefore, the user is required to have knowledge for identifying the type of paper; moreover, it is cumbersome for the user himself to input each time settings are made depending on the type of paper. Then, if there is an error with the settings, it is not possible to obtain an optimal image.

Now, Patent document 1 discloses a surfaceness discriminating device which includes a sensor which abuts against a recording material surface to scan the surface to discriminate the surfaceness of the recording material surface.

Patent document 2 discloses a printing apparatus which discriminates a paper type from a pressure value detected by a pressure sensor abutting against paper.

Patent document 3 discloses a recording material discriminating apparatus which discriminates a type of a recording material using reflected and transmitted lights.

Patent document 4 discloses a sheet material quality discriminating apparatus, wherein a material quality of a sheet material in movement is discriminated based on a reflected light amount which is reflected on a surface of the sheet material and a transmitted light amount which transmits through the sheet material.

Patent document 5 discloses an image forming apparatus which includes a determining unit which determines presence/absence of a recording material housed in a paper-supplying unit and presence/absence of the paper-supplying unit based on a detected output from a reflective-type optical sensor.

Patent document 6 discloses an image forming apparatus which irradiates light onto a recording medium to detect a light amount of two polarization components of the reflected light to discriminate the surfaceness of the recording medium.

PATENT DOCUMENT

Patent Document 1: JP2002-340518A
Patent Document 2: JP2003-292170A
Patent Document 3: JP2005-156380A
Patent document 4: JP10-160687A
Patent document 5: JP2006-062842A
Patent document 6: JP11-249353A However, minutely specifying an object without causing a high cost or a large size device is difficult.

DISCLOSURE CF THE INVENTION

According to an embodiment of the present invention, an optical sensor is provided, the optical sensor including an irradiating system which irradiates, toward a surface of a subject, a linearly polarized light in a first polarization direction from an incident direction which is slanted relative to a normal direction of the surface; a first photodetecting system including a first photodetector which is arranged on an optical path of a light which is specularly reflected from the subject; a second photodetecting system including an optical element which is arranged on an optical path of a light which is diffuse reflected from the subject within an incident face in the subject and which separates a linearly polarized component in a second polarizing direction which is orthogonal to the first polarizing direction and a second photodetector which receives a light separated by the optical element, wherein an angle of taking in the light in the first photodetector and an angle of taking in the light in the second photodetector are mutually different.

The optical sensor according to the present invention makes it possible to minutely specify an object without causing a high cost or a large size device.

BRIEF DESCRIPTION OF THE DRAWINGS

Other objects, features, and advantages of the present invention will become more apparent from the following detailed descriptions when read in conjunction with the accompanying drawings, in which:

FIGS. 25A and 25B are views for explaining an effect of ambient light;

BEST MODE FOR CARRYING OUT THE INVENTION

Figure 1:
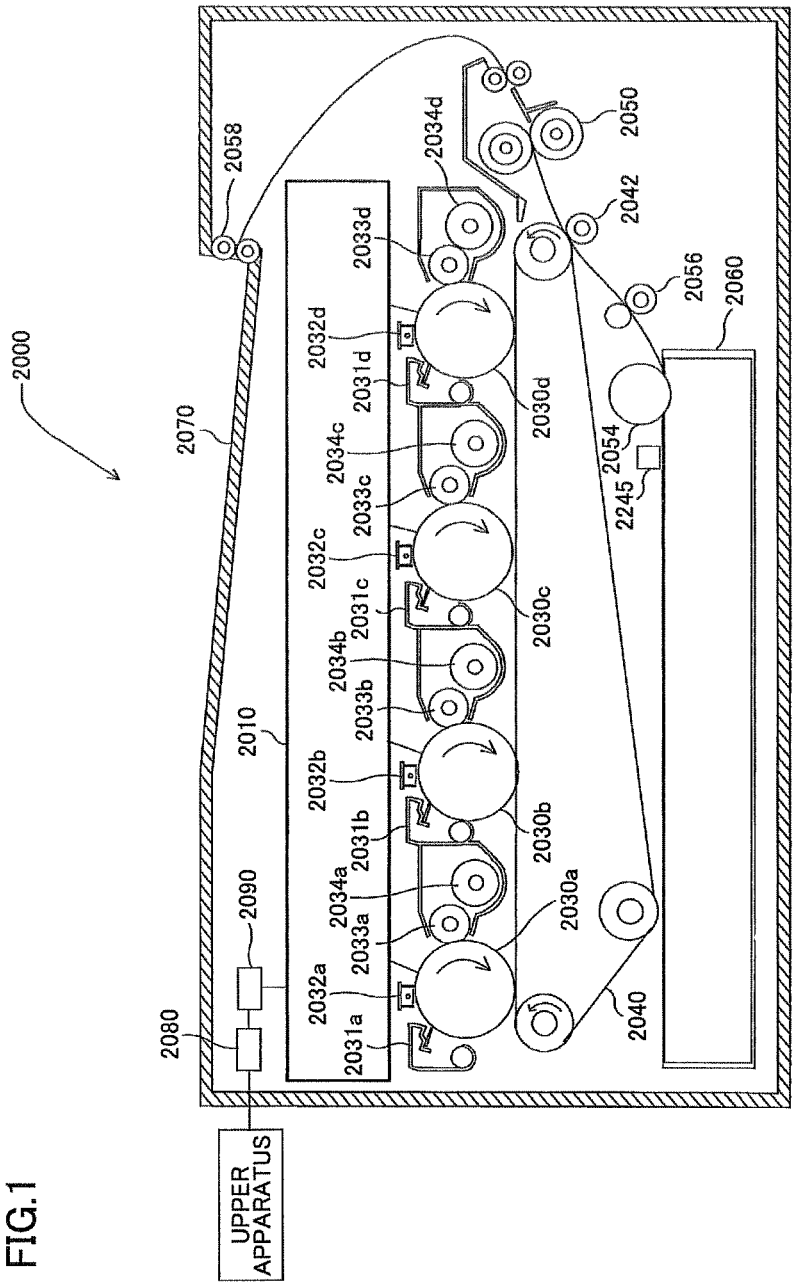
FIG. 1 is a diagram for explaining a schematic configuration of a color printer according to one embodiment of the present invention.

Below, one embodiment of the present invention is described based on FIGS. 1 to 13. FIG. 1 shows a schematic configuration of a color printer 2000 according to one embodiment.

This color printer 2000, which is a tandem-type multi color printer which forms a full-color image by overlapping four colors (black, cyan, magenta, yellow), includes an optical scanning apparatus 2010; four photoconductor drums (2030a, 2030b, 2030c, 2030d); four cleaning units (2031a, 2031b, 2031c, 2031d); four charging apparatuses (2032a, 2032b, 2032c, 2032d); four developing rollers (2033a, 2033b, 2033c, 2033d); a transfer belt 2040; a transfer roller 2042; a fixing apparatus 2050; a paper-feeding roller 2054; a paper-discharging roller 2058; a paper-feeding tray 2060; a paper-discharging tray 2070; a communications control apparatus 2080; an optical sensor 2245; and a printer control apparatus 2090, which exercises control of the above-described respective elements.

The communications control apparatus 2080 controls two-way communications with an upper-level apparatus (e.g., a personal computer) via a network, etc.

The printer control apparatus 2090 includes a CPU; a ROM in which are stored programs described in codes which can be decoded by the CPU and various data for use in executing the programs; an RAM, which is a working memory; an amplifying circuit; an A/D converting circuit which converts analog data into digital data, etc. Then, the printer control apparatus 2090 controls respective elements in response to a request from the upper-level apparatus and sends image information from the upper-level apparatus to the optical scanning apparatus 2010.

The photoconductor drum 2030a, the charging apparatus 2032a, the developing roller 2033a, and the cleaning unit 2031a are used as a set and make up an image forming station which forms a black image (also called below "a K station" for convenience).

The photoconductor drum 2030b, the charging apparatus 2032b, the developing roller 2033b, and the cleaning unit 2031b are used as a set and make up an image forming station which forms a cyan image (also called below "a C station" for convenience).

The photoconductor drum 2030c, the charging apparatus 2032c, the developing roller 2033c, and the cleaning unit 2031c are used as a set and make up an image forming station which forms a magenta image (also called below "an M station" for convenience).

The photoconductor drum 2030d, the charging apparatus 2032d, the developing roller 2033d, and the cleaning unit 2031d are used as a set and make up an image forming station which forms a yellow image (also called below "a Y station" for convenience).

The respective photoconductor drums have formed on a surface thereof a photosensitive layer. In other words, the surfaces of the respective photoconductor drums are respectively faces to be scanned. The respective photoconductor drums rotate in an arrow direction within a face in FIG. 1 by a rotating mechanism (not shown).

Each charging apparatus uniformly charges a surface of a corresponding photoconductor drum.

The optical scanning apparatus 2010 scans the respective surfaces of the photoconductor drums charged with light modulated for corresponding colors based on multi-color image information (black image information, cyan image information, magenta image information, yellow image information) from the printer control apparatus 2090. In this way, latent images which correspond to image information are formed on the respective surfaces of the photoconductor drums. Each of the latent images formed here moves in a direction of a corresponding developing roller in conjunction with rotation of the photoconductor drum.

In conjunction with the rotating, toner from a corresponding toner cartridge (not shown) is thinly coated in a uniform manner on a surface of the respective developing roller. Then, when coming into contact with a surface of the corresponding photoconductor drum, the toner on the surface of the respective developing roller is only transferred to a portion on the surface on which light has been irradiated and is attached thereto. In other words, the respective developing roller causes toner to be attached to a latent image formed on a surface of a corresponding photoconductor drum to visualize the image. Here, an image to which the toner is attached (a toner image) moves in a direction of the transfer belt 2040 in conjunction with rotating of the photoconductor drum.

The respective toner images of yellow, magenta, cyan, and black are successively transferred onto the transfer belt 2040 at a predetermined timing and are overlapped, so that multi-color images are formed.

Recording paper is contained in the paper-feeding tray 2060. The paper-feeding roller 2054 is arranged in the vicinity of the paper-feeding tray 2060 and causes the recording paper to be taken out from the paper-feeding tray 2060 sheet by sheet. The recording paper is sent out toward a gap between the transfer belt 2040 and the transfer roller 2042 at a predetermined timing. In this way, a toner image on the transfer belt 2040 is transferred to the recording paper. The recording paper is sent to the fixing apparatus 2050.

In the fixing apparatus 2050, heat and pressure are applied to the recording paper, which causes toner to be fixed onto the recording paper. This recording paper is sent to the paper-discharging tray 2070 via the paper-discharging roller 2058 and is stacked in order onto the paper-discharging tray 2070.

The respective cleaning units remove toner remaining on the surface of the corresponding photoconductor drum (remaining toner). The surface of the photoconductor drum with the remaining toner thereon having been removed again returns to a position which opposes the corresponding charging apparatus.

The optical sensor 2245 is used to specify a brand of recording paper contained within the paper-feeding tray 2060.

Figure 2:
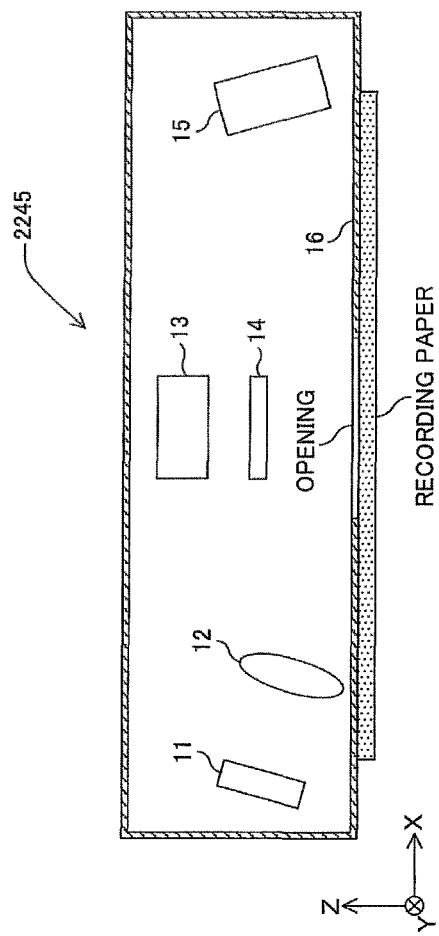
FIG. 2 is a diagram for explaining a configuration of an optical sensor in FIG. 1.

As shown in FIG. 2 as an example, this optical sensor 2245 includes an optical source 11, a collimating lens 12, two light receivers (13 and 15), a polarizing filter 14, and a dark box 16 in which the aforementioned elements are contained.

The dark box 16, which is a box member made of a metal (e.g., aluminum), has applied on a surface thereof black almite in order to reduce an impact of ambient light and stray light.

Here, in a XYZ three-dimensional orthogonal coordinate system, explanations are given with a direction which is orthogonal to a surface of the recording paper as a Z-axis direction and a plane which is parallel to the surface of the recording paper as a XY plane. Then, an optical sensor 2245 is arranged on a +Z side of the recording paper.

Figure 3:
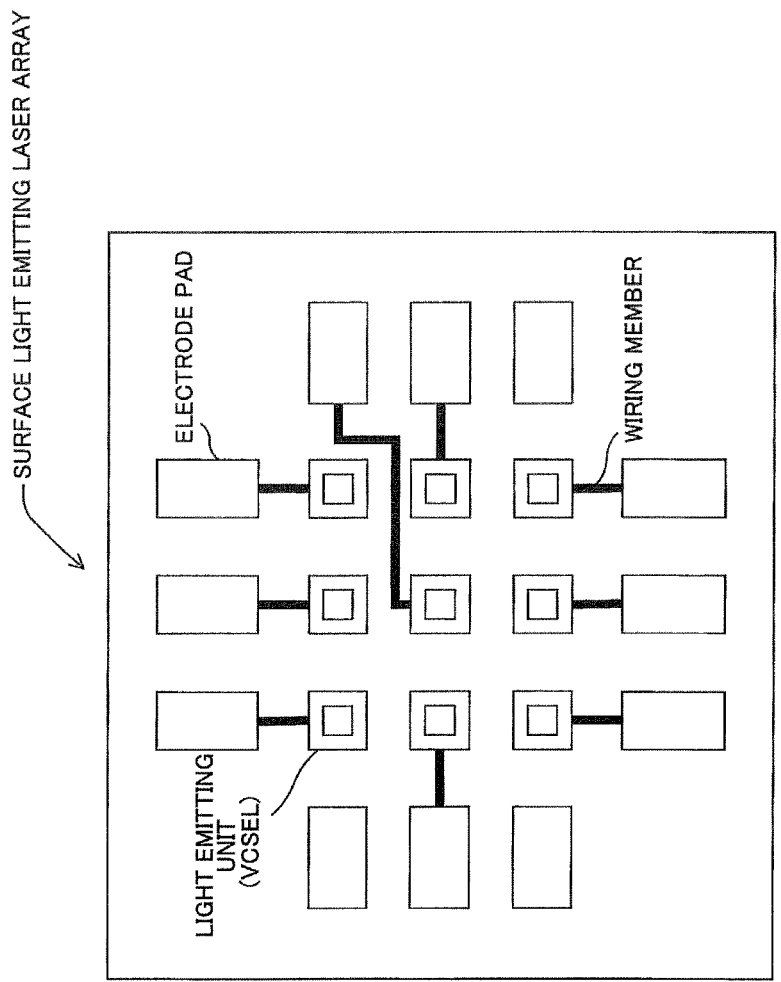
FIG. 3 is a diagram for explaining a surface light emitting laser array.
Figure 4:
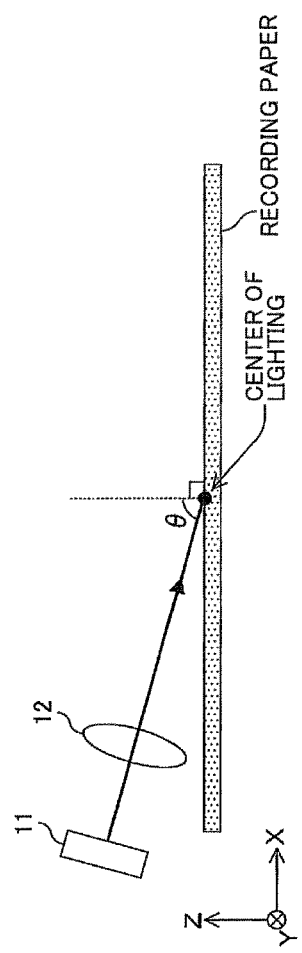
FIG. 4 is a view for explaining an angle of incidence of a light incident onto recording paper.

The optical source 11 includes multiple light emitting units formed on the same substrate. The respective light emitting units are vertical cavity surface emitting lasers (VCSELs). In other words, the light source 11 includes a surface emitting laser array (a VCSEL array). Here, as shown in FIG. 3 as an example, nine light emitting units are two-dimensionally aligned.

The light source 11 is arranged such that a linearly polarized light of S polarization is emitted onto the recording paper. Moreover, an incident angle $\theta$ (see FIG. 4) onto the recording paper of a light from the light source 11 is 80°.

Returning to FIG. 2, the collimating lens 12 is arranged on an optical path of the light emitted from the light source 11 and makes the light a generally parallel light. The light which passed through the collimating lens 12 passes through an opening provided in the dark box 16 to light the recording paper. Below, a center of a lighting region on a surface of the recording paper is abbreviated as "a center of lighting". Moreover, a light which has passed through the collimating lens 12 is also called "an irradiating light".

Now, when the light is incident onto a border face of a medium, a face which includes an incident beam and a normal of the border face that is erected at an incident point is called "an incident face". There, when the incident light includes multiple beams, an incident face exists for each beam; herein, for convenience of explanations, the incident face of the beam that is incident onto the center of lighting is to be called an incident face in the recording paper. In other words, a face parallel to an XZ plane that includes the center of lighting is an incident face on the recording paper.

The polarizing filter 14 is arranged on the +Z side of the center of lighting. This polarizing filter 14 is a polarizing filter which passes through a P polarized light and excludes an S polarized light. In lieu of the polarizing filter 14, a polarizing beam splitter may be used which has an equivalent function.

Figure 5:
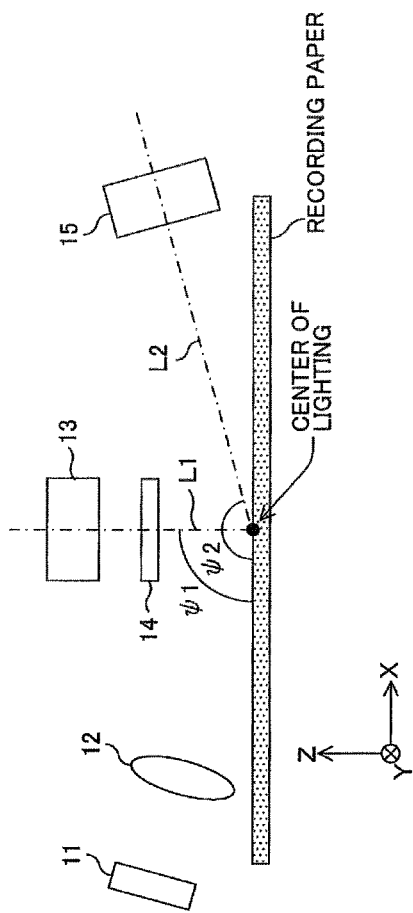
FIG. 5 is a view for explaining an arrangement location of two light receiving units.
Figure 6:
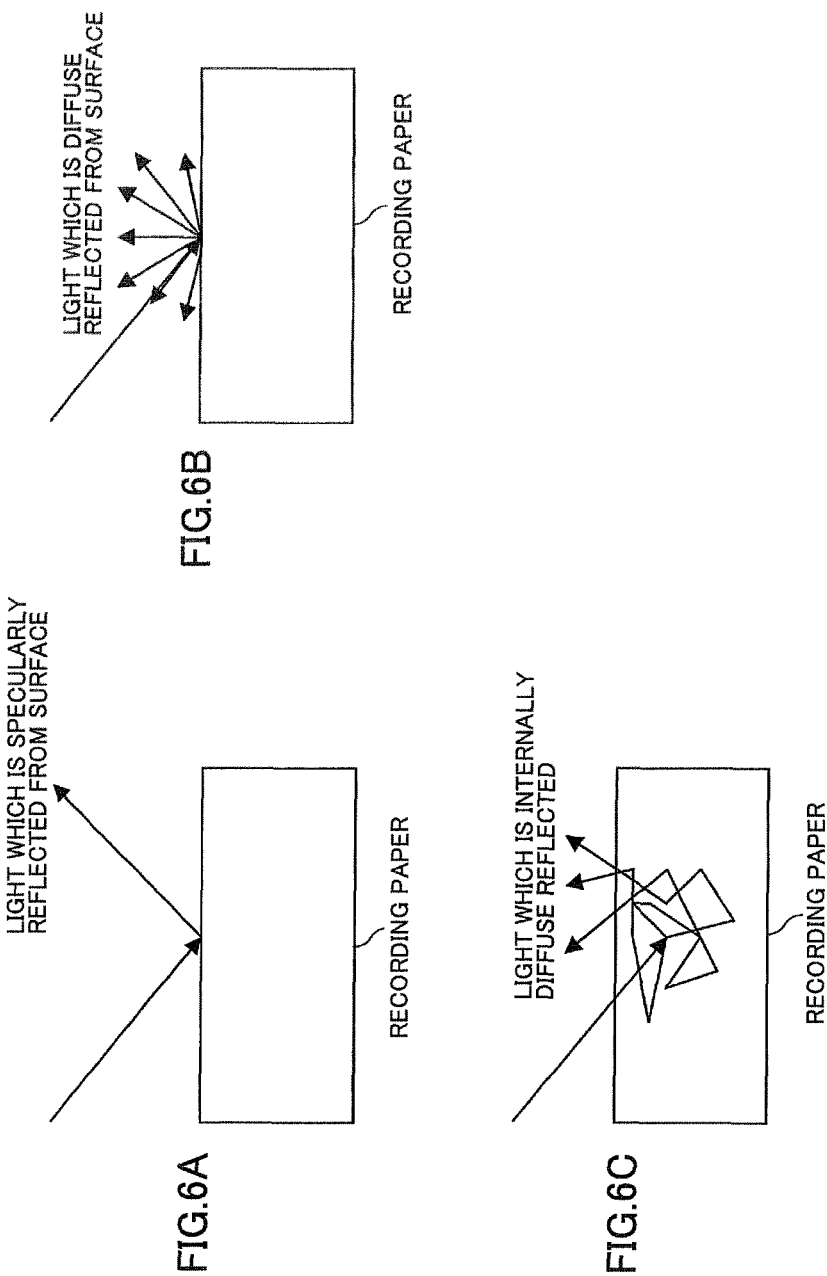
FIG. 6A is a diagram for explaining a light which is specularly reflected from a surface.
FIG. 6B is a diagram for explaining a light which is diffuse reflected from a surface.
FIG. 6C is a diagram for explaining a light which is internally diffuse reflected.
Figure 7:
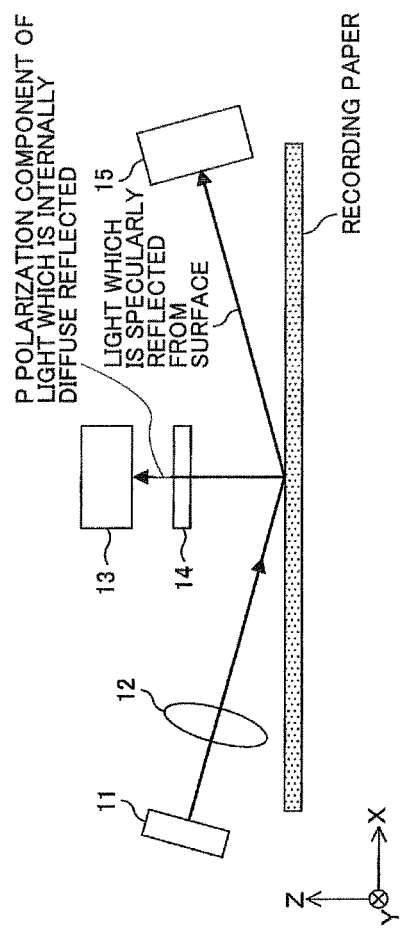
FIG. 7 is a diagram for explaining light received by each light receiver.

The light receiver 13 is arranged on the +Z side of the polarizing filter 14. Here, as shown in FIG. 5, an angle $\psi 1$ formed by a surface of the recording paper and a line L1 which links a center and the respective centers of the polarizing filter 14 and the light receiver 13 is 90°. In other words, the line L1 matches the normal of the recording paper surface in the center of lighting.

The light receiver 15 is arranged on the +X side of the center of lighting with respect to an X-axis direction. Then, an angle $\psi 2$ formed by a surface of the recording paper and a line L2 which links an illuminating center and the center of the light receiver 15 is 170°.

A center of the light source 11, the illuminating center, a center of the polarizing filter 14, a center of the light receiver 13, and a center of the light receiver 15 exist on almost the same plane.

Now, a reflected light from recording paper when the recording paper is illuminated thereon may be considered by dividing it into a reflected light which is reflected on a surface of the recording paper and a reflected light which is reflected internally within the recording paper. Moreover, the reflected light which is reflected on the surface of the recording paper may be considered by dividing it into a reflected light which is specularly reflected and a reflected light which is diffuse reflected. Below, for convenience, the reflected light which is specularly reflected on the surface of the recording paper is also called "a light which is specularly reflected from a surface", and a reflected light which is diffuse reflected on the surface of the recording paper is also called "a light which is diffuse reflected from a surface" (see FIGS. 6A and 6B).

A surface of the recording paper includes a plane portion and a slope portion, a proportion of which portions determine the smoothness of the recording paper surface. A light reflected on the plane portion becomes the light which is specularly reflected from the surface, while a light reflected on the slope portion becomes the light which is diffuse reflected from the surface. The light which is diffuse reflected from the surface is a reflected light which is completely diffuse reflected, so that a reflecting direction thereof is considered to be isotropic. Then, the higher the smoothness the larger a light amount of the light which is specularly reflected from the surface.

On the other hand, when the recording paper is a normal printing sheet, a light which is reflected from inside the recording sheet undergoes multiple-effect diffusion within fiber therein to yield only a diffuse reflected light. Below, for convenience of explanations, a reflected light from inside the recording paper is also called "a light which is internally diffuse reflected" (see FIG. 6C). The light which is internally diffuse reflected, in a manner similar to the light which is specularly reflected from the surface is a reflected light which is completely diffuse reflected, so that a reflecting direction thereof is considered to be isotropic.

A polarizing direction of the light which is specularly reflected from the surface and the light which is diffuse reflected from the surface is the same as a polarizing direction of the incident light. Now, in order for the polarizing direction to rotate on a surface of recording paper, the incident light must be reflected on a face which is slanted in a direction of the rotation relative to a direction of incidence thereof. Here, as the center of the light source, the center of lighting, and centers of the respective light receivers are on the same plane, the reflected light whose polarizing direction is rotated on the surface of the recording paper is not reflected in the direction of any of the light receivers.

On the other hand, the polarizing direction of the light which is internally diffuse reflected rotates relative to the polarizing direction of the incident light. This is considered to be due to the fact that it undergoes optical rotation while passing through the fiber and undergoing multiple-effect diffusion and the polarizing direction rotates.

Thus, the light which is diffuse reflected from the surface and the light which is internally diffuse reflected are incident onto the polarizing filter 14. As the polarizing direction of the light which is diffuse reflected from the surface is the same S polarization as the polarizing direction of the incident light, the light which is diffuse reflected from the surface is excluded by the polarizing filter 14. On the other hand, the polarizing direction of the light which is internally diffuse reflected is rotating relative to the polarizing direction of the incident light, so that a P polarized component which is included in the light which is internally diffuse reflected passes through the polarizing filter 14. In other words, the P polarized component which is included in the light which is internally diffuse reflected is received by the light receiver 13 (see FIG. 7). Below, for convenience of explanations, the P polarized component which is included in the light which is internally diffuse reflected is also called "a P polarized component of a light which is internally diffuse reflected". Moreover, the S polarized component which is included in the light which is internally diffuse reflected is also called "an S polarized component of a light which is internally diffuse reflected".

It has been confirmed by the present inventors, etc., that a light amount of the P polarized component of the light which is internally diffuse reflected has a correlation with a thickness and a density of the recording paper. This is due to the fact that the light amount of the P polarized component depends on a path length when it passes through the fiber of the recording paper.

Small portions of the light which is internally diffuse reflected and the light which is specularly reflected from the surface, and the light which is diffuse reflected from the surface are incident onto the light receiver 15. In other words, the light which is specularly reflected from the surface is primarily incident onto the light receiver 15.

The light receiver 13 and the light receiver 15 each output electrical signals (an opto-electric transducing signal) which correspond to the respective receiving light amounts to the printer control apparatus 2090.

Now, the reflected light amount from the recording paper is minute, and, in order to detect it at a general measuring resolution, it is preferable to amplify an output signal of the light receiver with an amplifying circuit, etc. However, elements such as an operational amplifier, a resistor, etc., which make up the amplifying circuit often have a temperature characteristic which differs individually, which could cause an amplification factor to differ from one output signal to another when multiple output signals are amplified.

Thus, for an element which makes up the amplifying circuit, it is preferable to use an array element in which multiple elements are sealed into one package. With the array element, variations are small for the temperature characteristics for each element. Thus, if the multiple output signals are amplified with the amplifying circuit which uses the array element, even when the amplification factor changes due to temperature fluctuations, etc., a rate of change thereof is constant for the respective output signals, making it possible to reduce the effect of the change of the amplification factor by performing a computation among the output signals (e.g., computing a ratio among the output signals).

In the general array element, the elements sealed within have the same characteristics (e.g., the same resistance value for a resistor array element), so that the amplification factor in the amplifying circuit which uses the array element is constant. Therefore, it is preferable for an amount of reflected light received by the respective light receivers to be of an equivalent magnitude so that, when the output signals of the respective light receivers are amplified by the printer control apparatus 2090, any output signal may fall within a dynamic range in the printer control apparatus 2090.

An amount of light reflected from the recording paper is largest for the light which is specularly reflected from the surface, and becomes smaller in the order of the light which is specularly reflected from the surface and the light which is internally diffuse reflected.

Figure 8:
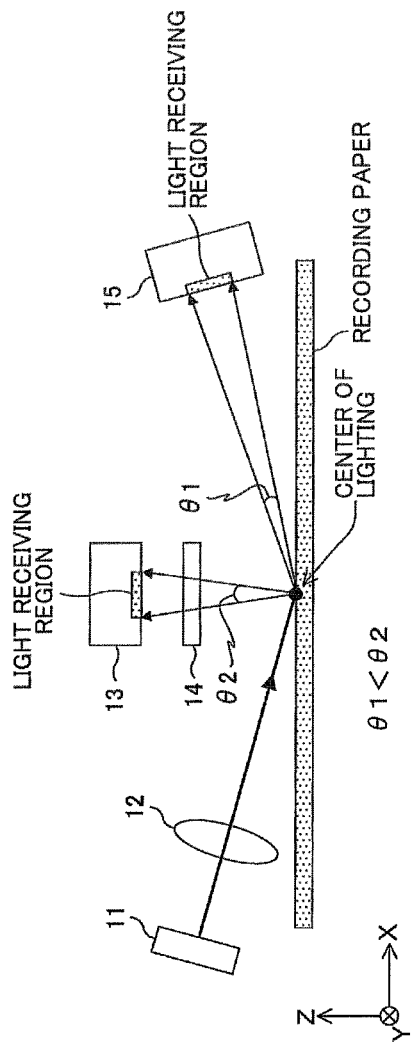
FIG. 8 is a diagram for explaining an acceptance angle of a light at each photodetector.

Thus, in the present embodiment, the light receiver 13 is provided at a position which is closer to the center of lighting relative to the light receiver 15 so that the amount of reflected light received in the light receiver 13 and the amount of reflected light received in the light receiver 15 are generally equivalent in magnitude, and, as shown in FIG. 8 as an example, an angle θ2 for taking in the reflected light in the light receiver 13 is set to be larger than an angle θ1 for taking in the reflected light in the light receiver 15. Here, the angle for taking in a reflected light in a light receiver is an angle formed by a straight line drawn from an edge of a light receiving region of a photodetector to an irradiating position at a subject, where, of lights reflected from the irradiating position, a light included in a range of the angle for taking in the reflected light is detected at the light receiving region.

Below, a signal level in an output signal in the light receiver 13 is called "S1", while a signal level in an output signal in the light receiver 15 is called "S2" that are amplified by the amplifying circuit of the printer control apparatus 2090 when a light from the light source 11 is irradiated onto the recording paper.

Here, for the recording paper of multiple brands which the color printer 2000 can handle, values of S1 and S2 are measured in advance for each brand of recording paper in a pre-shipping process such as an adjusting process, etc., results of which measurements are stored into a ROM for the printer control apparatus 2090 as "a recording paper discriminating table".

Figure 9:
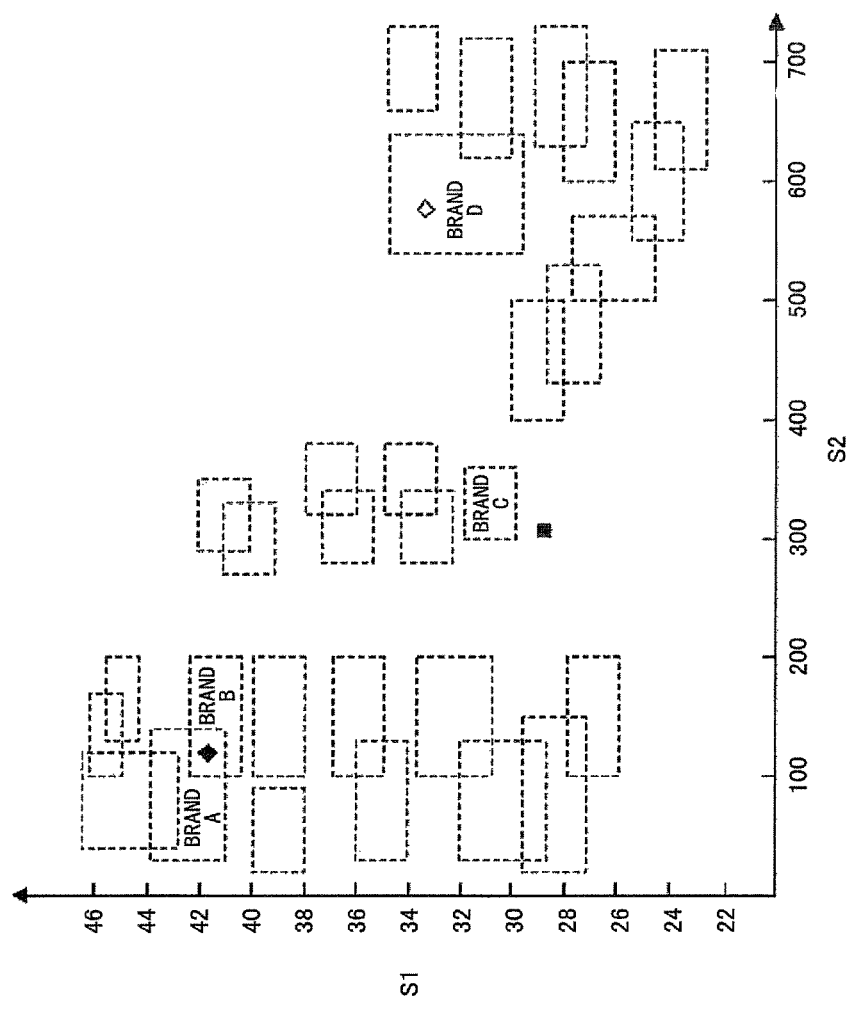
FIG. 9 is a diagram for explaining a relationship between S1 and S2, and recording paper brands.

FIG. 9 shows measured values of S1 and S2 for 30 brands of recording paper that are on the domestic market. A frame in FIG. 9 indicates a range of variance for the same brand. For example, if the measured values of S1 and S2 are white diamonds, it is specified as a brand D. Moreover, if the measured values of S1 and S2 are black squares, it is specified as C, which is the closest brand. Moreover, if the measured value of S1 and S2 are black diamonds, it may be a brand A or a brand B.

For example, in this case a difference between an average value and a measured value is computed for the brand A and a difference between an average value and a measured value is computed for the brand B, so that a brand with smaller computation results is specified. Moreover, a variance may be recalculated, assuming a brand to be the brand A, to include the measured value thereof and a variance may be recalculated, assuming a brand to be the brand B, to include the measured value thereof, and a brand with a smaller variance recalculated may be selected.

In the related art, a glossiness of a recording paper surface is detected from a light amount of a specularly reflected light, and a smoothness of the recording paper surface is detected from a ratio of the light amount of the specularly reflected light to the light amount of the diffuse reflected light in an attempt to identify the recording paper. On the other hand, in the present embodiment, not only the glossiness and the smoothness of the recording paper surface, but also information which also includes the thickness and the density, which are other characteristics of the recording paper are detected from the reflected light, so that the types of recording paper that can be identified have been expanded.

For example, it is difficult to distinguish between plain paper and mat coated paper with only information on the recording paper surface that is used in the related art identifying method. In the present embodiment, information on inside of the recording paper is added to information on the surface of the recording paper, making it possible to not only distinguish between plain paper and mat coat paper, but also among multiple brands of the plain paper and among multiple brands of the mat coat paper.

In other words, in the present embodiment, it is possible to specify a brand for the subject from multiple recording paper sets which differ in at least one of the glossiness, the smoothness, the thickness, and the density.

Moreover, for the recording paper of multiple brands which the color printer 2000 can handle, developing conditions and transfer conditions are determined which are optimal in the respective stations for each brand of recording paper in a pre-shipping process such as an adjusting process, etc., results of which determinations are stored into a ROM for the printer control apparatus 2090 as "a developing and transfer table".

When power of the color printer 2000 is turned on and when recording paper is supplied to the paper-feeding tray 2060, the printer control apparatus 2080 performs a process of discriminating paper types for the recording paper. The paper type discriminating process which is performed by the printer control apparatus 2090 is described below:

(1) Multiple light emitting units of the optical sensor 2245 are caused to emit light simultaneously;

(2) Values of S1 and S2 are determined from output signals of the light receiver 13 and the light receiver 15;

(3) The recording paper discriminating table is referred to and the brand for the recording paper is specified from the obtained values of S1 and S2; and (4) The specified brand for the recording paper is saved in a RAM, completing the paper type discriminating process.

When a printing job request is received from a user, the printer control apparatus 2090 reads a brand of recording paper saved in the RAM and developing conditions and transfer conditions which are optimal for the brand of the recording paper are determined from the developing and transfer table.

Then, the printer control apparatus 2090 controls the developing apparatus and the transfer apparatus of the respective stations in accordance with the optimal developing and transfer conditions. For example, the transfer voltage and the toner amount are controlled. In this way, a high quality image is formed onto the recording paper.

Now, a light which is diffuse reflected from the recording paper includes: A "a light which is diffuse reflected from the surface"; B "an S polarized component of a light which is internally diffuse reflected"; and C "a P polarized component of the light which is internally diffuse reflected".

In an apparatus which uses a related-art sensor, a type of recording paper is specified from two or three types based on a light amount of a diffuse reflected light (A+B+C). On the other hand, in the present embodiment, based on the light amount of the P polarized component of the light which is internally diffuse reflected, a type of recording paper is specified from at least 10 types. In other words, in the present embodiment, paper discriminating is performed with details which are at least five fold relative to the related art.

When an irradiating light is the S polarized light, a proportion of a light amount of a P polarized component of a light which is internally diffuse reflected that is in a light amount of the diffuse reflected light (A+B+C) is about 40% at a maximum. Moreover, an inexpensive polarizing filter such as one to be mounted in a general-purpose sensor, which has a low transmittance, is attenuated to about 80% with the polarizing filter. Thus, the P polarized component of the light which is internally diffuse reflected is attenuated when it is separated with the polarizing filter and becomes about 30% in substance.

The light amount of the P polarized component of the light which is internally diffuse reflected is attenuated to about 30% in substance of the diffuse reflected light (A+B+C), so that 3.3 times the related-art light amount is needed as the irradiating light amount. Moreover, in order to perform paper discriminating with details at five fold relative to the related art, it is necessary to irradiate an amount of light that is 3.3×5 times relative to the related art. Using a light receiving element with a high resolution makes it possible to achieve paper discriminating with details even with a light amount which is lower therethan, but leads to a higher cost.

For using a non-polarized light source such as an LED (Light-Emitting Diode), an S polarized light is irradiated onto the recording paper, so that, before irradiating, it is necessary to pass the light through a polarizing filter to make it a linearly polarized light (an S polarized light). Here, when a polarizing filter which is inexpensive as described above is used, an amount of light which is irradiated onto the recording paper becomes about 40% (=50% (a reduced proportion of the P polarized light)×80% (a proportion attenuated in the polarizing filter)).

Therefore, when the LED is used, an irradiating light amount which is at least 40 fold (=3.3×5/0.4) is necessary relative to the related art. However, the amount of irradiating light of the inexpensive related-art LED is about a few mWs (1 mW as a representative value), so that it is difficult to secure the amount of irradiating light that is 40 times thereof (at least 40 mW) with the LED.

On the other hand, a surface emitting laser array makes it possible to easily secure a desired irradiating light amount by lighting multiple light emitting units at the same time.

Moreover, in order to accurately detect a P polarized component of the light which is internally diffuse reflected, it is preferable that the following two light receiving conditions are satisfied:

(1) Detecting of the P polarized component of the light which is internally diffuse reflected is not performed in a direction in which at least a light which is specularly reflected from the surface is included.

This is due to the fact that, in practice, it is difficult to completely make the irradiating light only the S polarized light, so that a light reflected on the surface may also end up including the P polarized light component. Therefore, in a direction in which a light which is specularly reflected from the surface, a P polarized component, which is included in the irradiating light in the first place and which is reflected on the surface becomes larger than a P polarized component of the internally diffused reflected light. Thus, in case the polarizing filter 14 and the light receiver 13 are arranged in a direction in which a light which is specularly reflected from the surface is included, it is not possible to accurately detect an amount of reflected light in which information inside the recording paper is included.

Now, it is also possible to use a polarizing filter with a high extinction ratio in order to completely make the irradiating light only the S polarized light, but it leads to a higher cost.

(2) Detecting of the P polarized component of the internally diffuse reflected light is performed in a normal direction of a center of lighting in the recording paper.

This is due to the fact that the internally diffuse reflected light may be considered a complete diffuse reflection, so that the light amount reflected relative to the detecting direction may be approximated with a Lambert distribution and the reflected light amount is largest in a normal direction of the illuminating center. Thus, when the polarizing filter 14 and the light receiver 13 are arranged in a normal direction of the center of lighting, S/N is high and accuracy is highest.

Next, a method of suppressing a speckle pattern is described.

In a sensor which detects a surface condition of a printing sheet from a reflected light amount, it is preferable to use a semiconductor laser for a light source in order to improve an S/N, in which case a coherent light emitted from the semiconductor laser undergoes an irregular reflection at each point of a rough face such as a surface of recording paper, and mutual intervention therebetween causes a speckle pattern.

The speckle pattern differs depending on an irradiating area of a light, causing a variation in an amount of light received in the light receiver and leading to a decreased accuracy of discrimination. Thus, in the related art, an LED, etc., is generally used as a light source.

Figure 10:
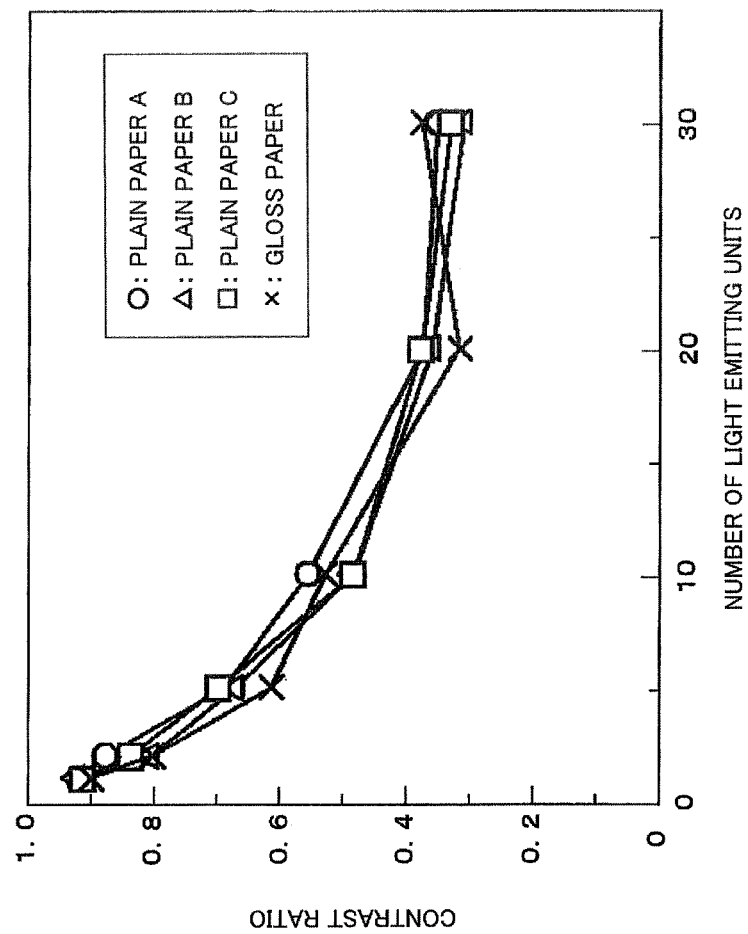
FIG. 10 is a view for explaining an effect of the number of light emitting units on a contrast ratio of a speckle pattern.

The present inventors used a vertical cavity surface emitting laser array (a VCSEL array) in which multiple light emitting units are two-dimensionally aligned, and determined a relationship between a contrast ratio of the speckle pattern and the number of light emitting units (see FIG. 10). Here, a value which normalizes a difference between a maximum value and a minimum value in an observation intensity of the speckle pattern is defined as a contrast ratio of the speckle pattern. Below, for convenience of explanations, the contrast ratio of the speckle pattern is also simply called "the contrast ratio".

The speckle pattern was observed using a beam profiler relative to a Y-axis direction (a diffuse direction) and the contrast ratio was calculated from the observed results by the beam profiler. For samples, three types of plain paper (Plain paper A, plain paper B, plain paper C) with the smoothnesses which are mutually different and a glossy paper were used. The plain paper A is plain paper with an Oken type smoothness of 33 seconds, the plain paper B is plain paper with an Oken type smoothness of 50 seconds, and the plain paper C is plain paper with an Oken type smoothness of 100 seconds.

From FIG. 10, it can be seen that there is a tendency for the contrast ratio to decrease when the number of light-emitting units increase. Moreover, this tendency does not depend on the paper type.

Furthermore, the present inventors have also conducted an experiment for confirming that the effect of reducing the contrast ratio is not due to an increase in the total light amount, but due to an increase in the number of light-emitting units.

Figure 11:
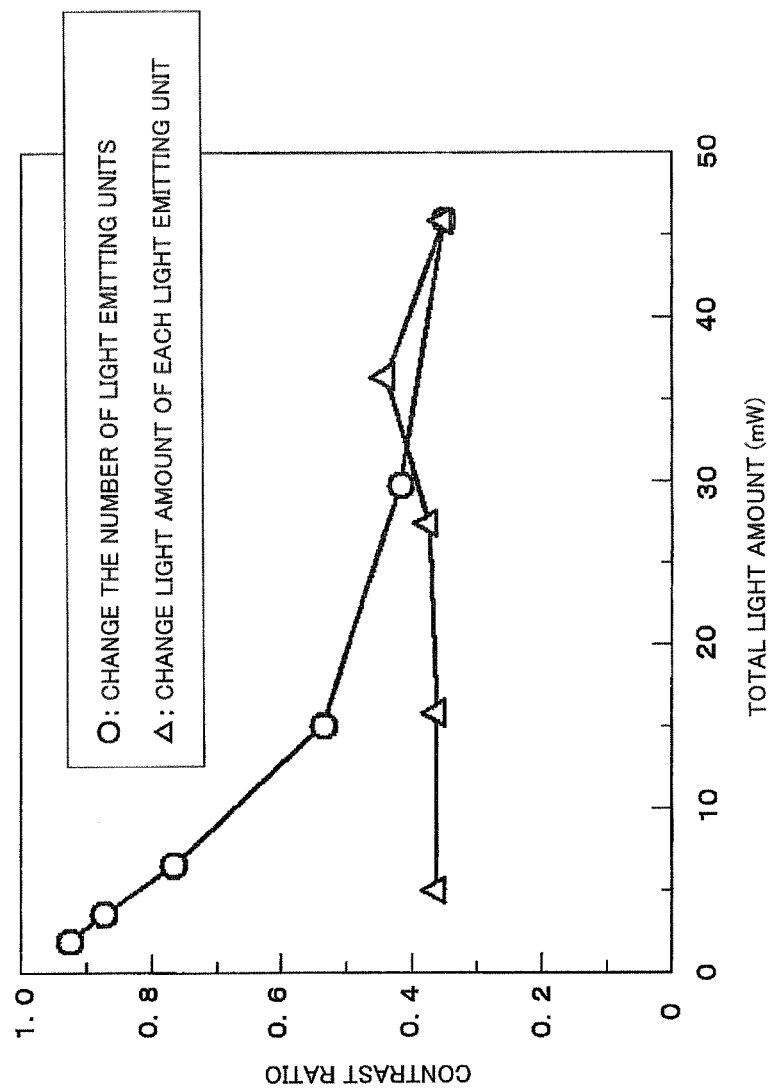
FIG. 11 is a view for explaining a relationship between a total light amount and the contrast ratio of the speckle pattern when the number of light emitting units is changed and when the light amount of each light emitting unit is changed.

FIG. 11 shows a relationship between the total light amount and the contrast ratio when the light amounts of the respective light-emitting units are made constant (at 1.66 mW) while changing the number of light emitting units and when the light amounts of the respective light-emitting units are changed while fixing the number of light-emitting units to 30.

When the light amount of each of the light-emitting units is changed while fixing the number of light-emitting units, the contrast ratio is constant regardless of the light amount, whereas when the number of light-emitting units is changed while fixing the light amount of each of the light-emitting units, the contrast ratio is large when the number of light-emitting units is small, and the contrast ratio decreases with an increase in the number of light-emitting units. In this way, it can be seen that an effect of reducing the contrast ratio is not due to an increase in the individual unit light amount, but due to an increase in the number of light-emitting units.

Moreover, the present inventors conducted an investigation on whether the speckle pattern may be suppressed by temporally changing a wavelength of a light emitted from the light source.

A vertical cavity surface emitting laser (a VCSEL) may control a wavelength of an emitted light with a drive current. This is due to the fact that, when the drive current changes, the reflectance changes due to a temperature change inside the vertical cavity surface emitting laser, so that an effective resonator length changes.

Figure 12:
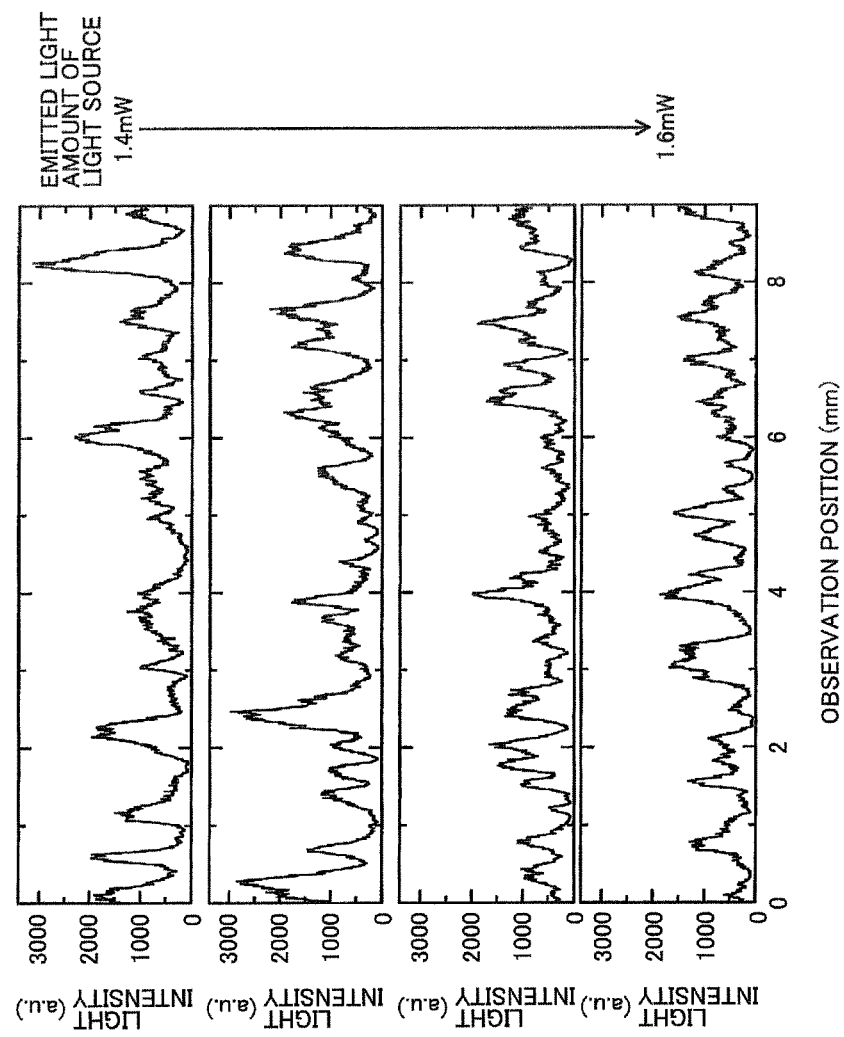
FIG. 12 is a view for explaining a light intensity distribution of the speckle pattern when a driving current of a light source is changed.

FIG. 12 shows a light intensity distribution obtained by observing with a beam profiler when a driving current of the light source 11 is changed to change an emitted light amount in a range of 1.4 mW to 1.6 mW. It may be seen from FIG. 12 that, with the change in the driving current, or in other words, with a change in a wavelength of a light emitted from the light source 11, the light intensity distribution changes.

Figure 13:
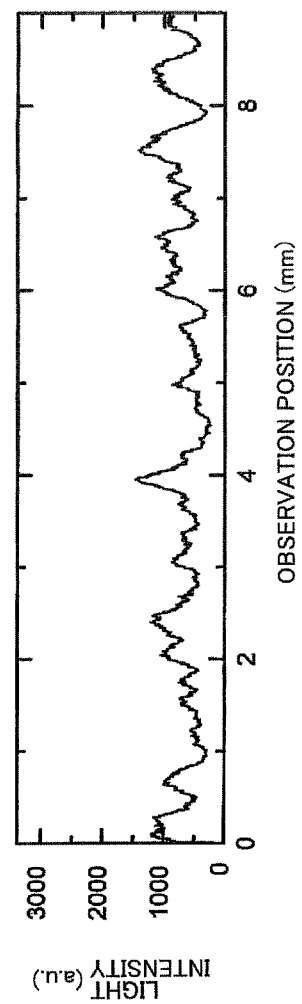
FIG. 13 is a view for explaining an effective light intensity distribution of the speckle pattern when the driving current of the light source is changed at high speed.
Figure 14:
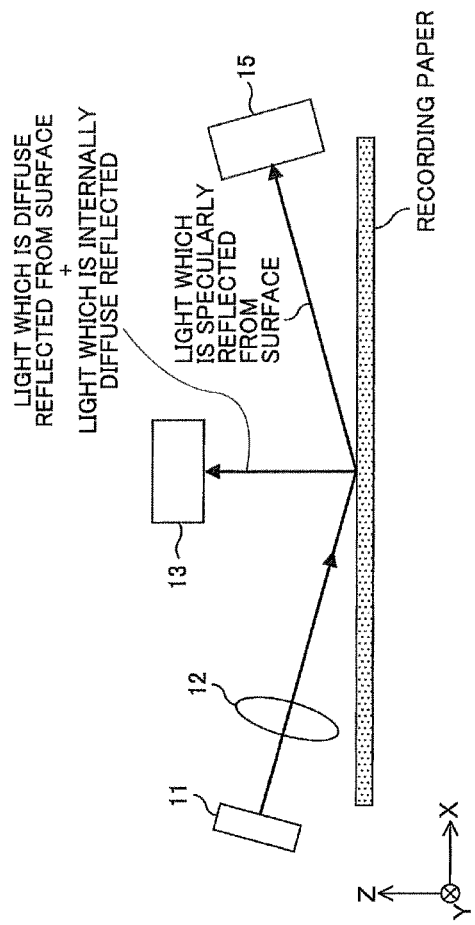
FIG. 14 is a view for explaining a Variation 1 of the optical sensor.

FIG. 13 shows an effective light intensity distribution when the driving current of the light source is changed at a high speed. The light intensity distribution is equivalent to an average value of light intensity distributions in multiple driving currents shown in FIG. 12. In this way, a contrast ratio when the driving current is changed at the high speed becomes 0.72, which is reduced from a contrast ratio of 0.96 when the driving current is kept constant.

In other words, it is seen that temporally changing a wavelength of an irradiating light suppresses a speckle pattern. Thus, the driving current of the surface emitting laser can be made a driving current whose current value temporally changes, such as a triangular waveform, to reduce the contrast ratio.

In the present embodiment, the light source 11 of the optical sensor 2245 includes a surface emitting laser array in which nine light-emitting units are two-dimensionally aligned, and a CPU of the printer control apparatus 2090 supplies a driving current having a triangular waveform to the surface emitting laser array. In this way, the speckle pattern is suppressed, making it possible to accurately detect a reflected light amount. Then, the accuracy of discriminating recording paper may be increased.

Now, in the surfaceness discriminating device disclosed in Patent document 1 and the printing apparatus disclosed in Patent document 2, the recording material surface could be damaged and a surface characteristic itself could be changed.

With the recording material discriminating apparatus disclosed in Patent document 3, only recording materials which differ in the smoothness could be discriminated, while recording materials which differ in the thickness but which have the same smoothness could not be discriminated.

With the sheet material quality discriminating apparatus disclosed in Patent document 4, discriminating is done based on a light amount of a specularly reflected light. In other words, a material quality of a sheet material is discriminated from an absolute light amount of the specularly reflected light, not taking into account of inside the subject.

With the image forming apparatus disclosed in Patent document 5, a light amount of a light reflected from a subject is detected in multiple directions. In this case as well, without taking into account of inside of the subject, the glossiness is detected from a ratio between a specularly reflected light and a diffuse reflected light and a paper type is discriminated.

With the image forming apparatus disclosed in Patent document 6, a specularly reflected light is divided into two polarization components for detecting, a smoothness of a surface of paper is determined from a light amount difference and a paper type is discriminated. In this case, polarization is used, but detecting is done in a direction in which the specularly reflected light is included; again, this also does not take into account of inside the subject.

In other words, with the sheet material quality discriminating apparatus disclosed in Patent document 4 and the image forming apparatuses disclosed in Patent documents 5 and 6, what can be discriminated is only a difference among uncoated paper, coated paper, and an OHP sheet, so that it is not possible to specify a brand necessary for high quality image forming.

In this way, in the related art, discriminating among the uncoated paper, the coated paper, and the OHP sheet is performed, so that discriminating at a brand level is not possible.

Moreover, while it is possible to install, for example, various sensors such as a temperature sensor, a sensor which detects a resistance value of a recording material, a sensor which detects a thickness of a recording material using a transmitting light, ultrasound, etc., separately from a reflective optical sensor to further segment a discriminating level, problems arise of the number of parts increasing, a high cost, and a large size.

A method of discriminating recording paper according to the present embodiment is a result of newly adding, to a related-art discriminating method, a method of discriminating by a light amount of an internal diffuse light in which is included information on inside of the recording paper that is not taken into account. In this case, information on density and thickness of recording paper in addition to a related-art glossiness (smoothness) of the recording paper surface may be obtained, making it possible to subdivide a discriminating level.

As is evident from the explanations in the above, in the optical sensor 2245 according to the present embodiment, the light source 11 and the collimating lens 12 make up an irradiating system of the present invention, the light receiver 15 makes up the first optical detecting system of the present invention, and the polarizing filter 14 and the light receiver 13 make up the second optical detecting system of the present invention.

As described above, the optical sensor 2245 according to the present embodiment includes the light source 11, the collimating lens 12, the light receiver 13, the polarizing filter 14, the light receiver 15, and the dark box 16, etc., in which these elements are housed.

The light receiver 13 primarily receives a P polarized component of a light which is internally diffuse reflected, while the light receiver 15 primarily receives a light which is specularly reflected from a surface. Then, the light receiver 13 is provided at a position which is closer to a center of lighting relative to the light receiver 15 such that an amount of reflected light received by the light receiver 13 and an amount of reflected light received by the light receiver 15 are generally equivalent in magnitude, making an angle θ2 of taking in a reflected light by the light receiver 13 larger than an angle θ1 of taking in a reflected light by the light receiver 15. In this case, it is possible to improve the accuracy of specifying a brand of recording paper.

The light source 11 includes a surface emitting laser array which includes multiple light emitting units. In this case, a polarizing filter for making an irradiating light a linearly polarized light is not necessary. Moreover, it becomes simple to make an adjustment for making the irradiating light the parallel light. Thus, reducing a size and a cost of the optical sensor can be achieved.

Moreover, in the surface emitting laser array, densely integrating multiple light emitting units, which are difficult to form with an LED, etc., used in the related art, becomes possible. Thus, all laser lights may be concentrated in the vicinity of an optical axis of a collimating lens, making it possible to make an angle of incidence constant to make multiple lights generally parallel and to easily realize a collimating optical system.

The printer control apparatus 2090 causes multiple light emitting units of the surface emitting laser array to emit light at the same time. Therefore, it is possible to increase a light amount of a P polarized component of an internally diffuse reflected light and to decrease the contrast ratio. Moreover, the printer control apparatus 2090 temporally changes a wavelength of a light emitted from the light source 11. Therefore, the speckle pattern may be suppressed.

Now, in the optical sensor 2245, it is possible to accurately separate a reflected light from inside recording paper that is weak and difficult to separate in the related art. The reflected light from inside the recording paper includes information on an internal condition of the recording paper.

Then, the printer control apparatus 2090 specifies a brand of recording paper based on an output signal of the light receiver 13 and an output signal of the light receiver 15. In other words, information on the internal conditions of the recording paper is added to improve to a level of discriminating a paper type, which is difficult in the related art.

Moreover, a component configuration is simple, without combining multiple types of sensors, making it possible to realize a small optical sensor at a low cost.

Now, the optical sensor 2245 makes it possible to more finely specify a brand of recording paper relative to the related art without leading to a high cost and a large size.

Then, the color printer 2000 according to the present embodiment is provided with the optical sensor 2245; as a result, a high quality image may be formed without leading to a high cost and a large size. Moreover, a printing failure due to a mistake in setting or the trouble of having to set manually in the related art may be resolved.

While a case is described that a light being irradiated onto recording paper is an S polarized light, it is not limited thereto, so that the light being irradiated onto the recording paper may be a P polarized light. In this case, a polarizing filter which transmits the S polarized light is used in lieu of the polarizing filter 14, and the light receiver 13 receives an S polarized component of the internally diffuse reflected light.

Moreover, in the above embodiment, if a discriminating level of the optical sensor 2245 is sufficient with a level which specifies either one of the non-coating paper, the coating paper, and the OHP sheet, the polarizing filter 14 is not necessary.

Figure 15:
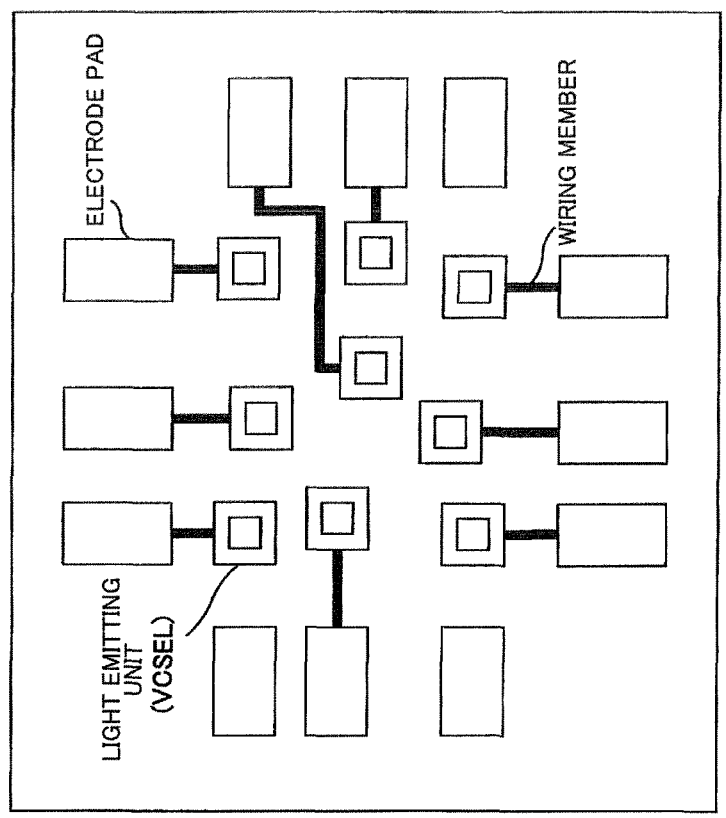
FIG. 15 is a diagram for explaining a surface light emitting laser array, wherein intervals of light emitting units thereof are not equal intervals.

Furthermore, in the above-described embodiment, multiple light emitting units of the surface emitting laser array may have at least some of light emitting unit intervals differing from the other light emitting unit intervals (See FIG. 15). In other words, intervals of neighboring light emitting units may differ.

Figure 16:
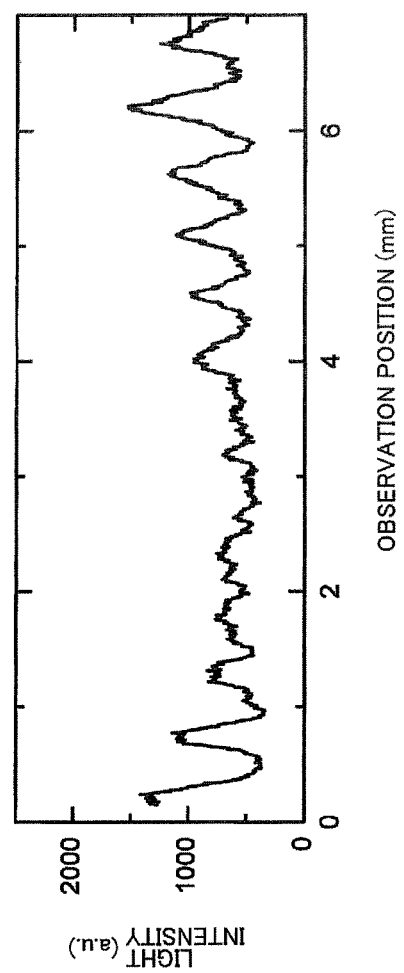
FIG. 16 is a diagram for explaining a light intensity distribution of a speckle pattern when the intervals of the light emitting units are equal intervals.

FIG. 16 shows a light intensity distribution which is obtained by observing, with a beam profiler, a speckle pattern when the intervals of the light emitting units are set as equal intervals in a light source which includes a surface emitting laser array in which five light emitting units are one dimensionally aligned. In this case, a periodic oscillation in a light intensity that corresponds to the regularity of a light emitting unit arrangement was confirmed and the contrast ratio was 0.64.

Figure 17:
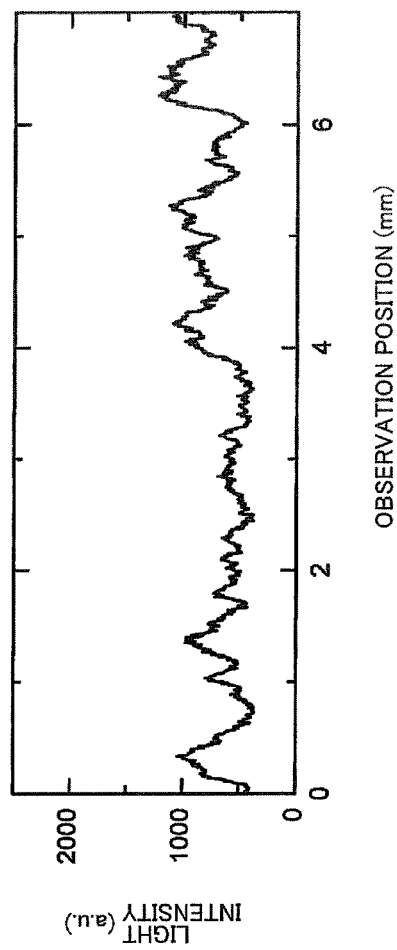
FIG. 17 is a diagram for explaining the light intensity distribution of the speckle pattern when the intervals of the light emitting units are not equal intervals.

Moreover, in a light source which includes a surface emitting laser array in which five light emitting units are one dimensionally aligned, a light intensity distribution which is obtained by observing, with a beam profiler, a speckle pattern when ratios of intervals of the light emitting units are set to be irregular as 1.0:1.9:1.3:0.7 is shown in FIG. 17. In this case, a periodic oscillation in the light intensity was suppressed and the contrast ratio was 0.56.

Now, making light emitting unit intervals in multiple light emitting units not equal intervals causes the regularity of the speckle pattern to be disturbed, making it possible to further reduce the contrast ratio.

Now, when an erroneous paper type discriminating could occur due to an impact of ambient light and stray light, a photodetecting system may be added.

Figure 18:
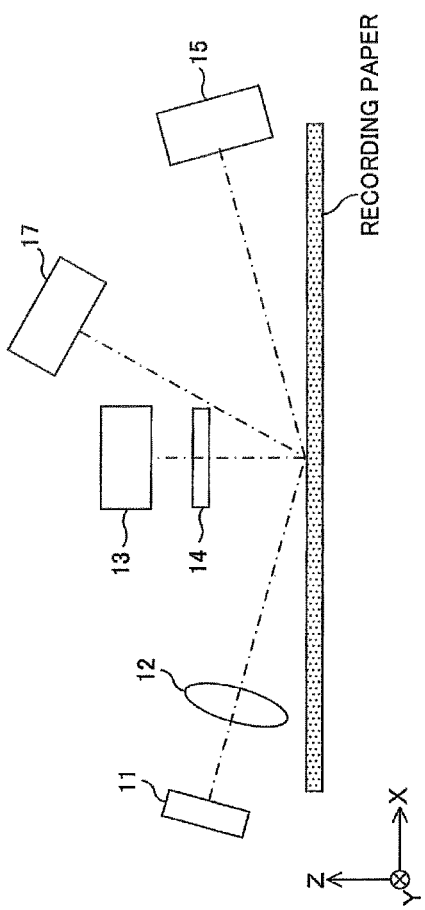
FIG. 18 is a first part of a view for explaining a Variation 2 of the optical sensor.
Figure 19:
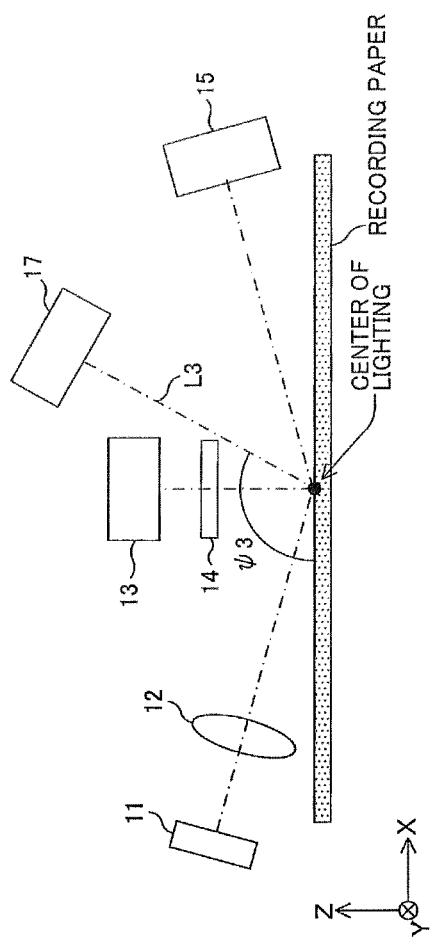
FIG. 19 is a second part of the view for explaining the Variation 2 of the optical sensor.

For example, as shown in FIG. 18, as a third photodetecting system, a light receiver 17 may also be included. This light receiver 17 is arranged at a position which receives a light which is diffuse reflected from a surface and an internally diffuse reflected light. A center of the light source 11, a center of lighting, a center of the polarizing filter 14, a center of the light receiver 13, a center of the light receiver 15, and a center of the light receiver 17 exist on almost the same plane. Then, an angle ψ3 which is formed by a surface of recording paper and a line L3 which links the center of lighting and the center of the light receiver 17 is 120° (see FIG. 19).

Moreover, so that an amount of reflected light received by the light receiver 17 and an amount of reflected light received by the light receiver 15 are generally equivalent in magnitude, the light receiver 17 is provided at a position which is closer to the center of lighting relative to the light receiver 15 and an angle of taking in the reflected light at the light receiver 17 is arranged to be larger than an angle of taking in the reflected light at the light receiver 15.

Below is described a paper type discriminating process which is performed by the printer control apparatus 2590 in the above-described case. Below, a signal level in an output signal of the light receiver 17 that is amplified by an amplifying circuit of the printer control apparatus 2090 when a light from the light source 11 is irradiated onto the recording paper is called "S3":

(1) Cause multiple light emitting units of the optical sensor 2245 to emit light at the same time;

(2) Determine values of S1, S2, and S3 from the output signals of the respective light receivers;

(3) Determine a value of S3/S2;

(4) Refer to a recording paper discriminating table and specify a brand of recording paper from the obtained values of S1 and S3/S2; and (5) Save the specified brand of the recording paper in a RAM, completing the paper type discriminating process.

In this case, with respect to multiple brands of recording paper that the color printer 2000 can handle, in a pre-shipping process such as an adjusting process, etc., in advance, values of S1 and S2/S3 are measured for each brand of recording paper and the measured results are stored in a ROM of the printer control apparatus 2090 as "the recording paper discriminating table".

Figure 20:
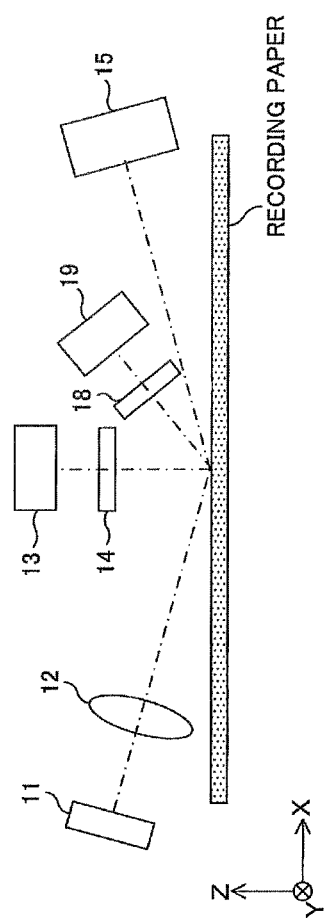
FIG. 20 is a first part of a view for explaining a Variation 3 of the optical sensor.

Moreover, as shown in FIG. 20, for example, as a third photodetecting system, a polarizing filter 18 and a light receiver 19 may further be included. The polarizing filter 18 may be arranged on an optical path of the light which is diffuse reflected from the surface and internally diffuse reflected light. This polarizing filter 18 is a polarizing filter which transmits a P polarized light and excludes an S polarized light. The light receiver 19 may be arranged on an optical path of the light which has passed through the polarizing filter 18. Then, the light receiver 19 receives a P polarized component of the internally diffuse reflected light.

Figure 21:
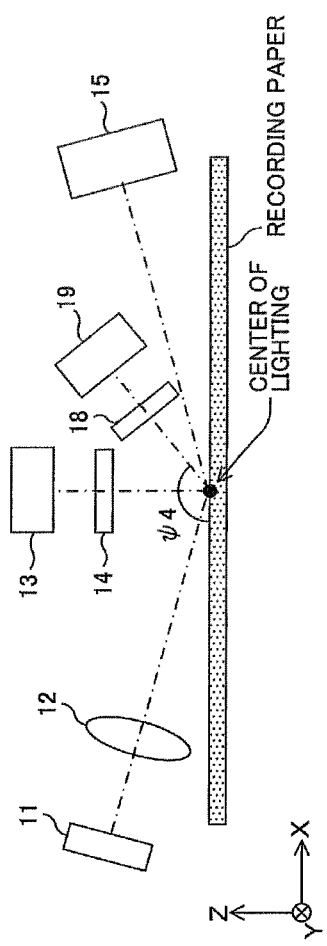
FIG. 21 is a second part of the view for explaining the Variation 3 of the optical sensor.

Moreover, the center of the light source 11, the center of lighting, the center of the polarizing filter 14, the center of the light receiver 13, the center of the light receiver 15, a center of the polarizing filter 18, and a center of the light receiver 19 exist on almost the same plane. Then, an angle γ4 which is formed by a surface of the recording paper and a line L4 which links the illuminating center and centers of the polarizing filter 18 and the light receiver 19 is 150° (see FIG. 21).

Moreover, so that an amount of reflected light received by the light receiver 19 and an amount of reflected light received by the light receiver 15 are generally equivalent in magnitude, the light receiver 19 is provided at a position which is closer to the center of lighting relative to the light receiver 15 and an angle of taking in the reflected light at the light receiver 19 is arranged to be larger than an angle of taking in the reflected light at the light receiver 15.

Below is described a paper type discriminating process which is performed by the printer control apparatus 2090 in the above-described case. Below, a signal level in an output signal of the light receiver 19 that is amplified by an amplifying circuit of the printer control apparatus 2090 when a light from the light source 11 is irradiated onto the recording paper is called "S4":

(1) Cause multiple light emitting units of the optical sensor 2245 to emit light at the same time;

(2) Determine values of S1, S2, and S4 from the output signals of the corresponding light receivers;

(3) Determine values of S4/S1 and S2;

(4) Refer to a recording paper discriminating table and specify a brand of recording paper from the obtained values of S2 and S4/S1; and (5) Save the specified brand of the recording paper in a RAM, completing the paper type discriminating process.

In this case, with respect to multiple brands of recording paper that the color printer 2000 can handle, in a pre-shipping process such a an adjusting process, etc., in advance, values of S2 and S4/S1 are measured for each brand of recording paper and the measured results are stored in a ROM of the printer control apparatus 2090 as "the recording paper discriminating table".

Figure 22:
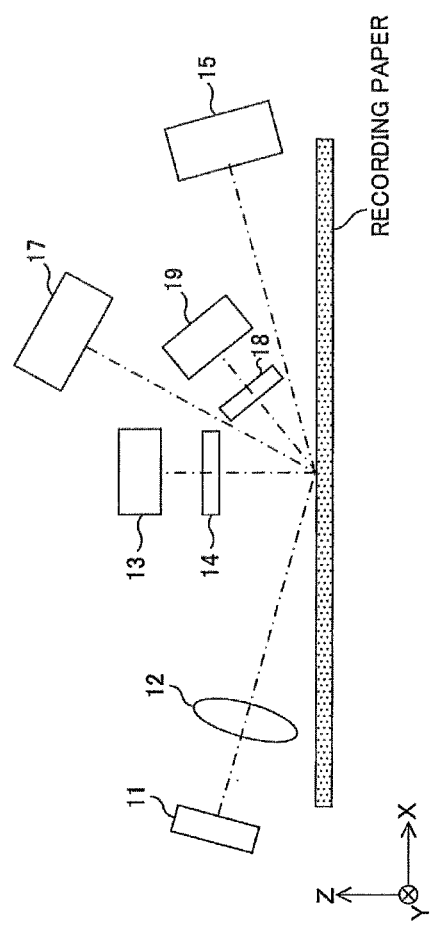
FIG. 22 is a first part of a view for explaining a Variation 4 of the optical sensor.
Figure 23:
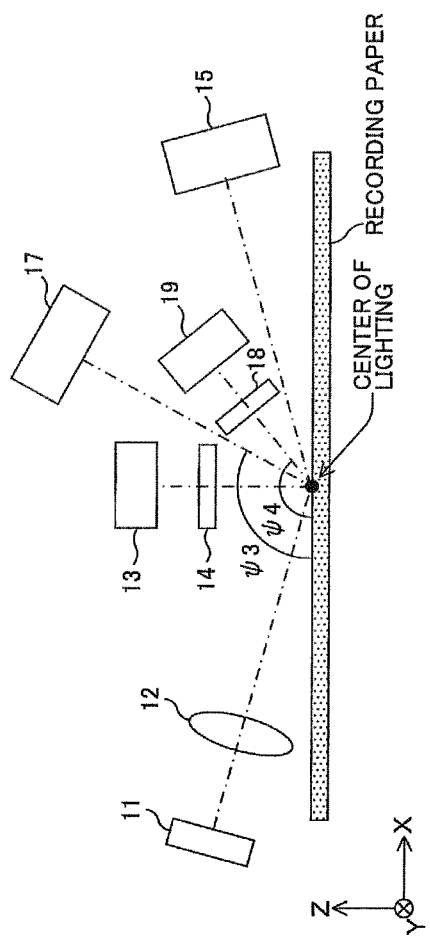
FIG. 23 is a second part of the view for explaining the Variation 4 of the optical sensor.

Moreover, for example, as shown in FIGS. 22 and 23, the light receiver 17, the polarizing filter 18, and the light receiver 19 may further be included. In other words, a third photodetecting system which is made up by the light receiver 17 and a fourth photodetecting system which is made up by the polarizing filter 18 and the light receiver 19 may further be included.

Below is described a paper type discriminating process performed by the printer control apparatus 2090 in this case.

Figure 24:
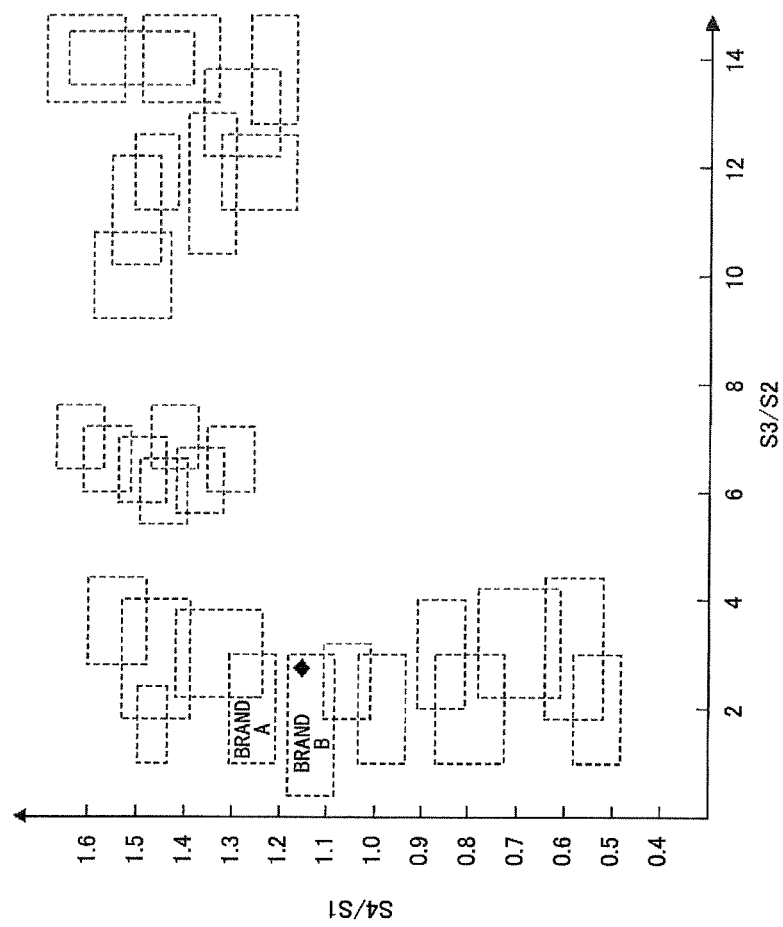
FIG. 24 is a diagram for explaining a relationship between S4/S1 and S3/S2, and recording paper brands.

(1) Cause multiple light emitting units of the optical sensor 2245 to emit light at the same time;

(2) Determine values of S1, S2, S3, and S4 from the output signals of the respective light receivers;

(3) Determine values of S4/S1 and S3/S2;

(4) Refer to a recording paper discriminating table and specify a brand of recording paper from the obtained values of S4/S1 and S3/S2 (see FIG. 24); and (5) Save the specified brand of the recording paper in a RAM, completing the paper type discriminating process.

In this case, with respect to multiple brands of recording paper that the color printer 2000 can handle, in a pre-shipping process such as an adjusting process, etc., in advance, values of S4/S1 and S3/S2 are measured for each brand of recording paper and the measured results are stored in a ROM of the printer control apparatus 2090 as "the recording paper discriminating table".

In this way, multiple light receiving systems which respectively detect diffuse lights which are mutually reflected in different directions are provided and recording paper is discriminated using computed values such as a ratio detected at each light receiving system to make it possible to perform discrimination accurately even in the presence of ambient light or stray light.

Moreover, in this case, the printer control apparatus 2090 may roughly narrow down the paper types using S1 and S2 and use S4/S1 and S3/S2 to specify the brand of the recording paper.

Here, while S4/S1 is used as a method of computing using S4 and S1, it is not limited thereto. Similarly, for a method of computing using S2 and S3, it is not limited to S3/S2.

FIGS. 25A and 25B show results of investigating an impact of an ambient light for a case of discriminating a paper type using only S1 and S2 and for a case of discriminating a paper type using S4/S1 and S3/S2. As shown in FIG. 25A, for the case of discriminating the paper type using only S1 and S2, a presence of the ambient light causes a detected value at each light receiving system to increase, which could cause erroneous paper type discriminating. On the other hand, as shown in FIG. 25B, for the case of discriminating the paper type using S4/S1 and S3/S2, even a presence of the ambient light causes almost no change in S4/S1 and S3/S2 relative to when there is no ambient light, making it possible to perform correct paper type discriminating.

In this case, the third photodetecting system may include multiple light receivers. Moreover, the fourth photodetecting system may include multiple polarizing filters and light receivers.

For example, when the third photodetecting system includes two light receivers and the fourth photodetecting system includes two sets of polarizing filters and light receivers, assuming output levels of respective light receivers of the third photodetecting system of "S3" and "S5" and output levels of respective light receivers of the fourth photodetecting system of "S4" and "S6" that have been amplified by the amplifying circuit of the printer control apparatus 2090, paper type discriminating may be performed using a value of (S4/S1+S6/S1) and a value of (S3/S2+S5/S2). Moreover, paper type discriminating may be performed using a value of S4/S1, a value of S6/S1, a value of S3/S2, and a value of S5/S2.

As a matter of course, "a recording paper discriminating table" in accordance with a method of computing used in paper type discriminating is created in advance in a pre-shipping process such as an adjusting process, etc., and is stored in a ROM of the printer control apparatus 2090.

Now, in this case, it is not necessary to make output signal levels of all photodetecting systems equivalent. For example, when an output signal of the first photodetecting system which detects a specularly reflected light is amplified by a different amplifying circuit, it suffices to make output signal levels of the second to the fourth photodetecting systems equivalent.

Figure 26:
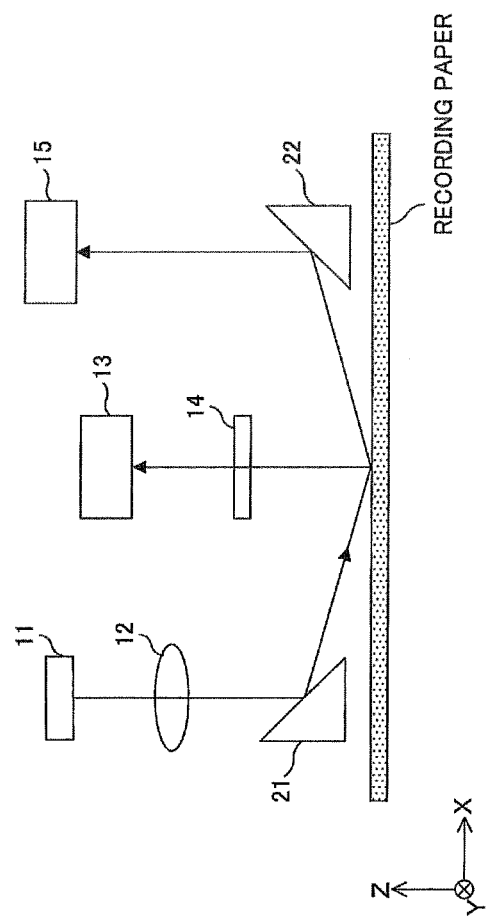
FIG. 26 is a view for explaining a Variation 5 of an optical sensor.

Moreover, in the above-described embodiment, as shown in FIG. 26 as an example, the optical sensor 2245 may further include two mirrors (21, 22).

Here, the light source 11 emits a light in a direction which is parallel to the Z axis and the collimating lens 12 is arranged such that an optical axis becomes parallel to the Z axis.

Then, the mirror 21 bends an optical path of a light which passes through the collimating lens 12 such that an angle of incidence at the recording paper becomes 80°.

The mirror 22, which is a mirror equivalent to the mirror 21, is arranged at a position which opposes the mirror 21 across an opening portion relative to an X-axis direction. Then, a light path of a light which is specularly reflected from a surface from the recording paper is bent such that a proceeding direction thereof becomes parallel to the Z axis.

Then, the light receiver 15, which is arranged on the +Z side of the mirror 22, receives a light which is specularly reflected from a surface, an optical path of which light is bent by the mirror 22. An angle of taking in by the light receiver 15 is equal to the above-described angle θ1 of taking in.

This case makes a member which supports the light source 11 and the collimating lens 12 and the light receiver 15 respectively for which a slant is not necessary and may simplify an electrical circuit. In this way, a reduction of cost and size may be facilitated.

Even when three or more light receivers are provided, a proceeding direction of a light which moves toward each light receiver is made to be a direction parallel to a Z axis with a mirror to facilitate a reduction of size of an optical sensor.

Moreover, in the present embodiment, while a case is described of varying a distance from a center of lighting to the light receiver 13 and a distance from the center of lighting to the light receiver 15 to vary an angle of taking in a reflected light at the light receiver 13 and an angle of taking in a reflected light at the light receiver 15, the method is not limited thereto.

Figure 27:
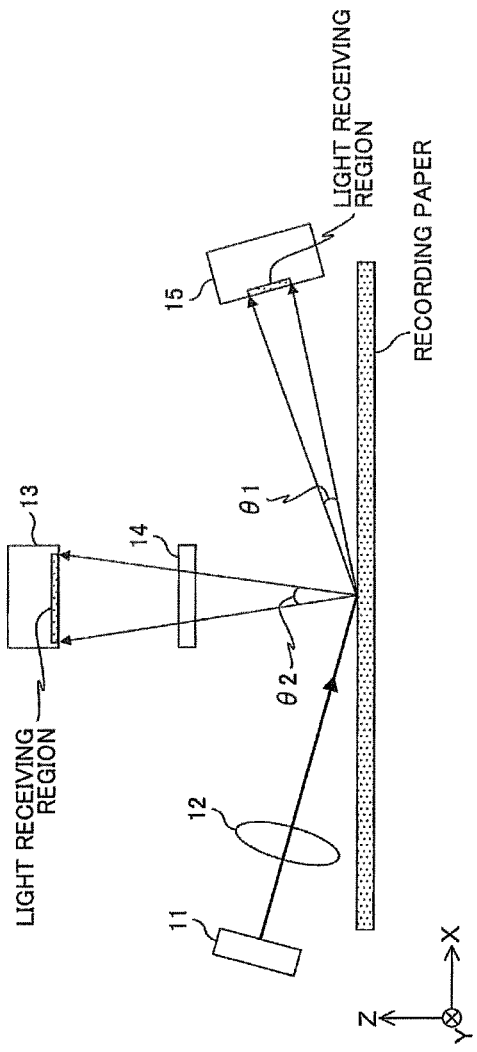
FIG. 27 is a view for explaining a Variation 6 of the optical sensor.

For example, a size (a light receiving diameter) of a light receiving region at the light receiver 13 may be varied from a size (a light receiving diameter) of a light receiving region at the light receiver 15 to vary an angle of taking in a reflected light at the light receiver 13 from an angle of taking in a reflected light at the light receiver 15 (see FIG. 27).

Figure 28:
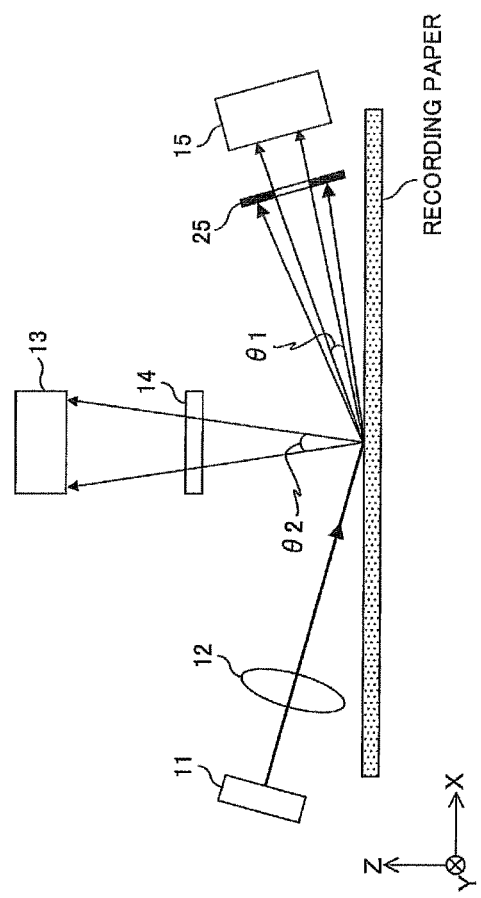
FIG. 28 is a view for explaining a Variation 7 of the optical sensor.

Moreover, as shown in FIG. 28 as an example, in front of the light receiver 15 may be arranged an opening member 25 which includes an opening of a predetermined size and which excludes a part of the reflected light in a surrounding of the opening.

Figure 29:
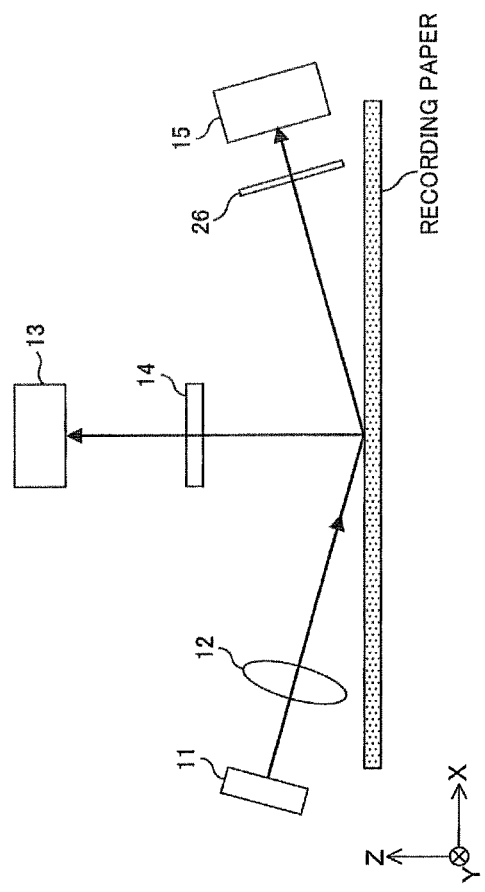
FIG. 29 is a view for explaining a Variation 8 of the optical sensor.

Moreover, as shown in FIG. 29 as an example, in front of the light receiver 15 a light attenuating filter (an ND filter) 26 may be arranged. In this case, depending on a light attenuation ratio of the light attenuating filter 26, the light receiver 15 may be provided at a position which is closer to the center of lighting relative to the light receiver 13.

Moreover, in the above-described embodiment, when the photodiode is used in each photodetector, wiring and mounting may be performed such as to make the anode side of the photodiode common. This makes it possible to make a ground level of the photodetectors common and to make a power supply of an operational amplifier a single power supply when amplification is performed by the operational amplifier.

The printer control apparatus 2090 includes an A/D converting circuit which A/D converts an amplified signal, etc., as well as an amplifying circuit. The power supply for powering the operational amplifier may be made a single power supply to share the power supply with other circuits and to simplify the overall configuration. This is preferable from cost and size reduction viewpoints. While the anode side is made common in order that a non-inverting amplifying circuit is used as an amplifying circuit, it is not necessarily limited thereto.

Moreover, in the above-described embodiment, while a case is described of the light source 11 including 9 light emitting units, it is not limited thereto.

Figure 30:
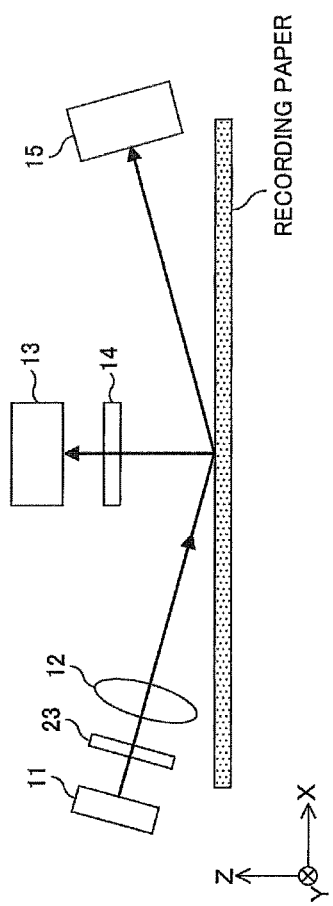
FIG. 30 is a view for explaining a Variation 9 of the optical sensor.

Furthermore, in the above-described embodiment, while a case is described of a linearly polarized light being emitted from the light source 11, it is not limited thereto. In this case, as shown in FIG. 30 as one example, a polarizing filter 23 becomes necessary for making an irradiating light an S polarized light.

Moreover, in the above-described embodiment, it is more preferable that a collimating lens is arranged in front of each light receiver. In this case, it is possible to reduce fluctuations in received light amount at each light receiver.

For an optical sensor which discriminates recording paper based on a reflected light amount, reproducibility of measurement is important. In the optical sensor which discriminates recording paper based on the reflected light amount, a measuring system is installed on the assumption that a measuring face and a surface of the recording paper are on the same plane at the time of measurement. However, due to reasons of deflection, vibration, etc., the surface of the recording paper becomes slanted or rises relative to the measuring face, so that a case may occur such that the measuring face and the surface of the recording paper are not on the same plane. In this case, the reflected light amount changes, so that stable and detailed discriminating becomes difficult. Here, a specular reflection is described as an example.

Figure 31A:
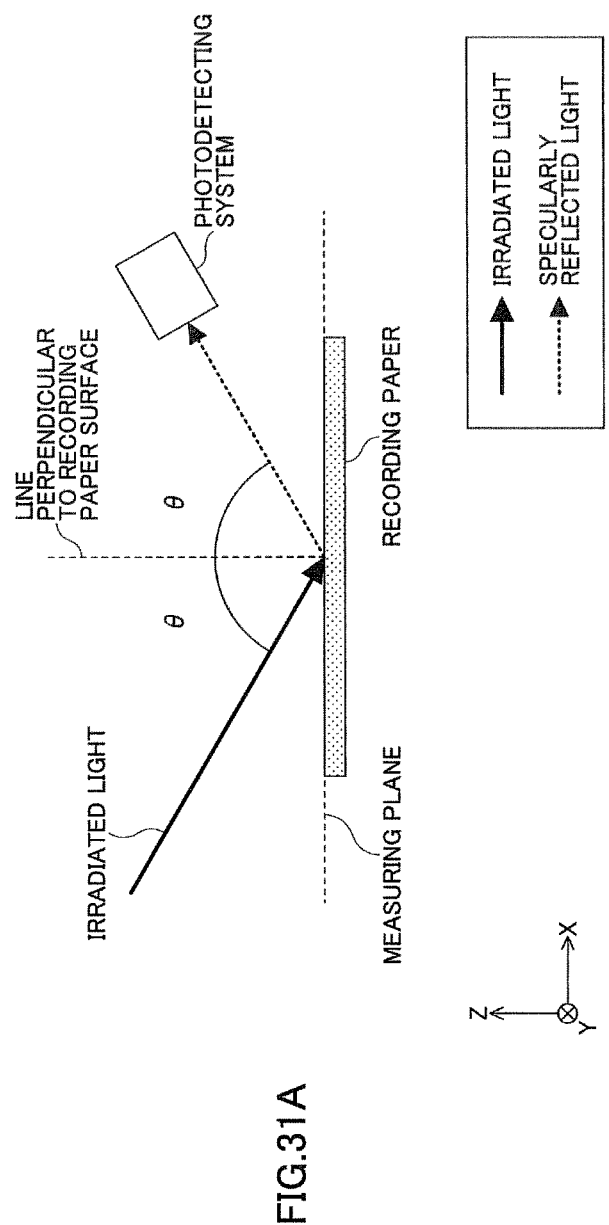
FIGS. 31A to 31C are views for explaining a change in a light amount detected due to an offset in a measuring plane and a recording paper surface.

FIG. 31A shows a case when a measuring face and a recording paper surface are on the same plane. Here, the photodetecting system may receive a specularly reflected light.

Figure 31B:
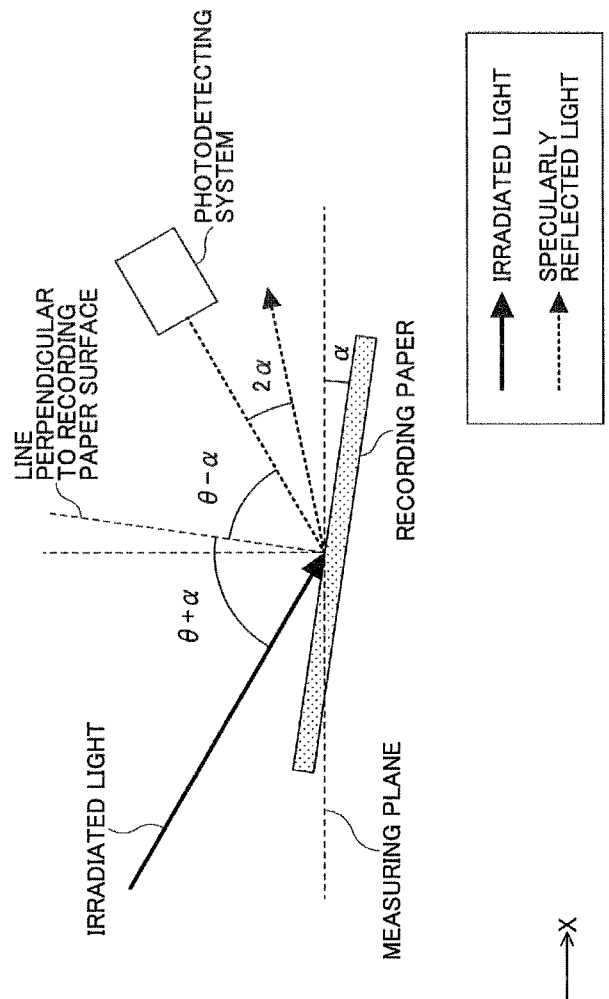

FIG. 31B shows a case in which the recording paper surface is slanted by an angle α relative to the measuring face. Here, when a positional relationship between a light irradiating system and a photodetecting system is the same as the case in FIG. 31A, the photodetecting system is to receive a light in a direction which is offset by 2α from a specularly reflecting direction. A reflected light intensity distribution has moved with the offset, so that, assuming a distance between a center location of the irradiating region and the photodetecting system of L, the photodetecting system is to receive a light at a position which is offset by L times tan 2α from the specularly reflected light receiving position. Moreover, an actual angle of incidence is offset by α from a specified angle of incidence of θ, causing a reflectance from the recording paper to change. Therefore, a change occurs in a detected light amount, consequently causing detailed discriminating to be difficult.

Figure 31C:
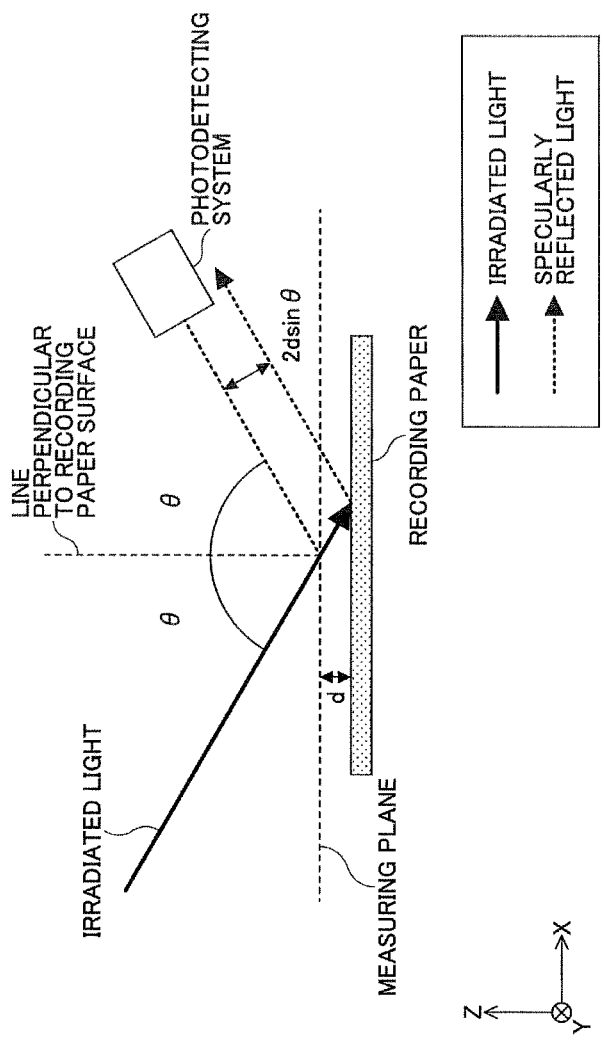

Moreover, FIG. 31C shows a case in which the recording paper surface is offset relative to a measuring plane by d in a height direction or in other words in a Z-axis direction relative to the measuring face. Here, when a positional relationship between a light irradiating system and a photodetecting system is the same as the case in FIG. 31A, the reflected light intensity distribution has moved with the offset, so that the photodetecting system is to receive a light at a position which is offset by 2d×sin θ from the specularly reflected light receiving position. Therefore, a change occurs in a detected light amount, consequently causing detailed discriminating to be difficult.

Cases of FIGS. 31B and 31C can be handled by arranging a collimating lens in front of a photodetecting system relative to a moving amount such that the photodetecting system surely detects a specularly reflected light and collimating is performed even when the reflected light intensity distribution has moved.

Alternatively, problems in a case where the recording paper surface is not on the same plane as the measuring face may be overcome by using a photodiode (PD) with a sufficiently large light receiving region for a light receiver or by decreasing a beam diameter of an irradiating light.

Moreover, a PD which is made into an array may be used for the light receiver to provide a configuration which includes a light receiving region which is sufficiently large relative to a moving amount of the reflected light intensity distribution. In this case, even when the reflected light intensity distribution has moved, a maximum signal of signals detected by the respective PDs may be made a signal for the specularly reflected light. Moreover, when the PD is made into the array, light receiving regions of individual PDs may be made small to reduce fluctuations in output due to an offset between the center of the light receiving region and the specularly reflected light to perform a more accurate detection.

Here, a specular reflection has been described for convenience of explanations; for surface diffuse reflection and internal diffuse reflection, while a change in a detected light amount also occurs due to an offset between the measuring face and the recording paper surface, such problems may be handled in the same manner as the case of the specular reflection.

Moreover, in the above-described embodiment, a processing apparatus may be provided in the optical sensor 2245, so that a part of processes in the printer control apparatus 2090 may be done by the processing apparatus.

Moreover, while a case with one paper-feeding tray has been described in the above-described embodiment, it is not limited thereto, so that there may be multiple paper-feeding trays. In this case, one optical sensor 2245 may be provided for each paper-feeding tray.

Moreover, in the above-described embodiment, a brand of recording paper may be specified during conveying. In this case, the optical sensor 2245 may be arranged in the vicinity of the conveying path. For example, the optical sensor 2245 may be arranged in the vicinity of the conveying path between the paper-feeding roller 2504 and the transfer roller 2042.

Furthermore, the subject to be discriminated by the optical sensor 2245 is not to be limited to the recording paper.

While a case of the color printer 200 as an image forming apparatus has been described in the above-described embodiment, it is not limited thereto. For example, it may be a laser printer which forms a monochrome image. Moreover, it may be an image forming apparatus other than a printer; for example, it may be a copying machine, a facsimile machine, or a multi-functional machine having these functions integrated therein.

Moreover, while a case is described of the image forming apparatus having four photoconductor drums in the present embodiment, it is not limited thereto. For example, it may be a printer having five photoconductor drums.

Furthermore, while an image forming apparatus is described in which a toner image is transferred onto recording paper from the photoconductor drum via a transfer belt in the above-described embodiment, it is not limited thereto, so that it may be an image forming apparatus in which the toner image is directly transferred from the photoconductor drum to the recording paper.

Moreover, the optical sensor 2245 is also applicable to an image forming apparatus which ejects ink onto recording paper to form an image.

Figure 32:
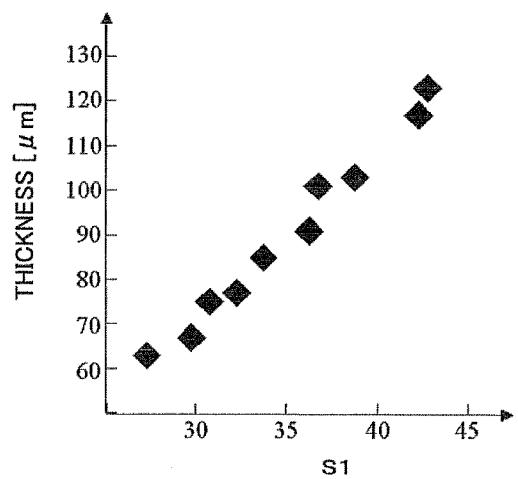
FIG. 32 is a diagram for explaining a relationship between a thickness and S1.

The optical sensor 2245 may be applied to detecting a thickness of a subject (see FIG. 32). A related-art thickness sensor has a transmission type configuration, so that optical systems need to be respectively arranged in both directions between which a subject is always placed. Thus, a supporting member, etc., are necessary. On the other hand, with the optical sensor 2245, a thickness is detected with only a reflected light, so that an optical system may be arranged only on one side of the subject. Then, it is possible to reduce the number of parts, making it possible to achieve a low cost and a small size. Thus, it is optimal for installation within an image forming apparatus which requires detecting the thickness of the subject.

Figure 33:
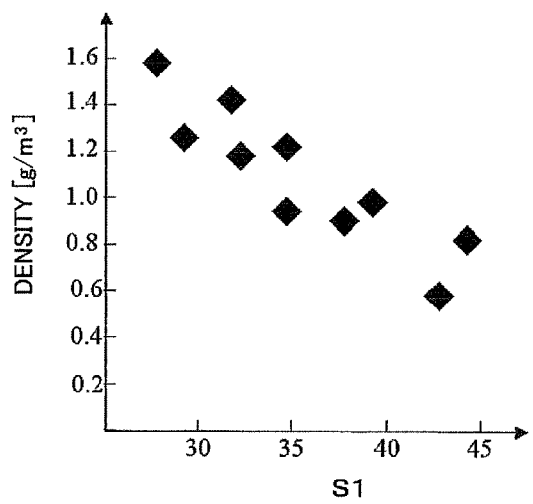
FIG. 33 is a diagram for explaining a relationship between a density and S1.

Moreover, the optical sensor 2245 may be applied to detecting a density of a subject (see FIG. 33). A related-art density sensor has a transmission type configuration, so that optical systems need to be respectively arranged in both directions between which a subject is always placed. Thus, a supporting member, etc., are necessary. On the other hand, with the optical sensor 2245, a density is detected with only a reflected light, so that an optical system may be arranged only on one side of the subject. Then, it is possible to reduce the number of parts, making it possible to achieve a low cost and a small size. Thus, it is optimal for installation within an image forming apparatus which requires detecting the density of the subject.

The present application is based on Japanese Priority Application No. 2012-032259 filed on Feb. 17, 2012, the entire contents of which are hereby incorporated by reference.

The invention claimed is:

1. An optical sensor, comprising:
   an irradiating system which irradiates, toward a surface of a subject, a linearly polarized light in a first polarization direction from an incident direction which is slanted relative to a normal direction of the surface;
   a first photodetecting system including a first photodetector which is arranged on an optical path of a light which is specularly reflected from the subject;
   a second photodetecting system including an optical element which is arranged on an optical path of a light which is diffuse reflected from the subject within an incident face in the subject and which separates a linearly polarized component in a second polarizing direction which is orthogonal to the first polarizing direction and a second photodetector which receives a light separated by the optical element, wherein
   an angle of taking in the light in the first photodetector and an angle of taking in the light in the second photodetector are mutually different, wherein an angle of taking in light of a photodetector is an angle formed by a light receiving region of the photodetector and a center of an illuminated area at the surface of the subject.

2. The optical sensor as claimed in claim 1, wherein a distance from an irradiating position in the subject to the second photodetector is shorter than a distance from an irradiating position in the subject to the first photodetector.

3. The optical sensor as claimed in claim 1, wherein a light receiving region of the second photodetector is larger than a light receiving region of the first photodetector.

4. The optical sensor as claimed in claim 1, wherein the first photodetecting system includes a shielding member which is arranged in front of the first photodetector and which shields a part of a light reflected from the subject.

5. The optical sensor as claimed in claim 1, wherein the optical element and the second photodetector are arranged on an optical path of a light which is diffuse reflected in the normal direction of the surface of the subject.

6. The optical sensor as claimed in claim 1, further comprising:
   a third photodetecting system which includes at least one photodetector arranged on the optical path of the light which is diffuse reflected from the subject within the incident face in the subject; and
   a processing unit which specifies the subject based on an output of the second photodetector and a ratio of an output of the first photodetector and the at least one photodetector of the third photodetecting system.

7. An optical sensor as claimed in claim 1, further comprising:
   a third photodetecting system including at least one optical element which is arranged on the optical path of the light which is diffuse reflected from the subject within the incident face in the subject and which transmits a linearly polarized component in the second polarizing direction and at least one photodetector which receives a light which is transmitted through the at least one optical element; and
   a processing unit which specifies the subject based on an output of the first photodetector and a ratio of an output of the second photodetector and the at least one photodetector of the third photodetecting system.

8. An image forming apparatus which forms an image on a recording medium, comprising:
   the optical sensor claimed in claim 1, which optical sensor discriminates the recording medium as the subject; and
   an adjusting apparatus which specifies a brand of the recording medium based on an output of the optical sensor and adjusts an image forming condition in accordance with the specified brand.

9. The optical sensor as claimed in claim 1, further comprising:
   a third photodetecting system which includes at least one photodetector arranged on the optical path of the light which is diffuse reflected from the subject within the incident face in the subject;
   a fourth photodetecting system including at least one optical element which is arranged on the optical path of the light which is diffuse reflected from the subject within the incident face in the subject and which transmits a linearly polarized component in the second polarizing direction and at least one photodetector which receives a light which is transmitted through the at least one optical element; and a processing unit which specifies the subject based on a ratio of an output of the first photodetector and the at least one photodetector of the third photodetecting system and a ratio of an output of the second photodetector and the at least one photodetector of the fourth photodetecting system.

10. The optical sensor as claimed in claim 9, wherein a relationship between the at least one photodetector of the third photodetecting system and the at least one photodetector of the fourth photodetecting system is similar to a relationship between the first photodetector and the second photodetector.

11. An optical sensor, comprising:
an irradiating system which irradiates, toward a surface of a subject, a linearly polarized light in a first polarization direction from an incident direction which is slanted relative to a normal direction of the surface;
a first photodetecting system including a first photodetector which is arranged on an optical path of a light which is specularly reflected from the subject;
a second photodetecting system including an optical element which is arranged on an optical path of a light which is diffuse reflected from the subject within an incident face in the subject and which separates a linearly polarized component in a second polarizing direction which is orthogonal to the first polarizing direction and a second photodetector which receives a light separated by the optical element, wherein
an angle of taking in the light in the first photodetector and an angle of taking in the light in the second photodetector are mutually different;
a third photodetecting system which includes at least one photodetector arranged on the optical path of the light which is diffuse reflected from the subject within the incident face in the subject;
a fourth photodetecting system including at least one optical element which is arranged on the optical path of the light which is diffuse reflected from the subject within the incident face in the subject and which transmits a linearly polarized component in the second polarizing direction and at least one photodetector which receives a light which is transmitted through the at least one optical element; and
a processing unit which specifies the subject based on a ratio of an output of the first photodetector and the at least one photodetector of the third photodetecting system and a ratio of an output of the second photodetector and the at least one photodetector of the fourth photodetecting system.

12. The optical sensor as claimed in claim 11, wherein a relationship between the at least one photodetector of the third photodetecting system and the at least one photodetector of the fourth photodetecting system is similar to a relationship between the first photodetector and the second photodetector.

\* \* \* \* \*